(12) United States Patent
Aharoni et al.

(10) Patent No.: US 7,279,172 B2
(45) Date of Patent: Oct. 9, 2007

(54) TREATMENT OF AUTOIMMUNE CONDITIONS WITH COPOLYMER 1 AND RELATED COPOLYMERS

(75) Inventors: Rina Aharoni, Rehovot (IL); Dvora Teitelbaum, Rehovot (IL); Ruth Arnon, Rehovot (IL); Michael Sela, Rehovot (IL); Masha Fridkis-Hareli, Cambridge, MA (US); Jack L. Strominger, Lexington, MA (US)

(73) Assignees: Yeda Research and Development Co., Ltd., Rehovot (IL); President and Fellows of Harvard College, Cambridge, MA (US)

( * ) Notice: Subject to any disclaimer, the term of this patent is extended or adjusted under 35 U.S.C. 154(b) by 1095 days.

(21) Appl. No.: 09/768,872

(22) Filed: Jan. 23, 2001

(65) Prior Publication Data

US 2002/0055466 A1 May 9, 2002

Related U.S. Application Data

(63) Continuation of application No. PCT/US99/16747, filed on Jul. 23, 1999.

(60) Provisional application No. 60/108,184, filed on Nov. 12, 1998, provisional application No. 60/106,350, filed on Oct. 30, 1998, provisional application No. 60/102,960, filed on Oct. 2, 1998, provisional application No. 60/101,825, filed on Sep. 25, 1998, provisional application No. 60/093,859, filed on Jul. 23, 1998.

(51) Int. Cl.
*A61K 38/02* (2006.01)

(52) U.S. Cl. .................. 424/280.1; 424/278.1; 424/810; 514/2; 514/12; 530/806

(58) Field of Classification Search ............... 530/350; 514/12, 2, 866, 885, 886, 903; 424/184.1, 424/810, 278.1, 280.1
See application file for complete search history.

(56) References Cited

U.S. PATENT DOCUMENTS

| | | |
|---|---|---|
| 3,849,550 A | 11/1974 | Teitelbaum et al. |
| 4,594,409 A | 11/1974 | Hayashi et al. |
| 3,991,210 A | 11/1976 | Shea |
| 4,129,666 A | 12/1978 | Wizerkaniuk |
| 4,339,431 A | 7/1982 | Gaffar |
| 5,204,099 A | 4/1993 | Barbier et al. |
| 5,554,372 A | 9/1996 | Hunter et al. |
| 5,583,031 A | 12/1996 | Stern |
| 5,591,629 A | 1/1997 | Rodriguez et al. |
| 5,623,052 A | 4/1997 | McLean et al. |
| 5,627,206 A | 5/1997 | Hupe et al. |
| 5,668,117 A | 9/1997 | Shapiro et al. |
| 5,719,296 A | 2/1998 | Acton, III et al. |
| 5,734,023 A | 3/1998 | Bishwajit et al. |
| 5,800,808 A | 9/1998 | Konfino et al. |
| 5,858,964 A | 1/1999 | Aharoni et al. |
| 5,886,156 A | 3/1999 | McLean et al. |
| 5,958,972 A | 9/1999 | Hupe et al. |
| 5,965,600 A | 10/1999 | Sato et al. |
| 5,981,589 A | 11/1999 | Konfino et al. |
| 6,024,981 A | 2/2000 | Khankari et al. |
| 6,048,898 A | 4/2000 | Konfino et al. |
| 6,054,430 A | 4/2000 | Konfino et al. |
| 6,162,800 A | 12/2000 | Dolle et al. |
| 6,214,791 B1 | 4/2001 | Arnon et al. |
| 6,342,476 B1 | 1/2002 | Konfino et al. |
| 6,362,161 B1 | 3/2002 | Kontino et al. |
| 6,514,938 B1 | 2/2003 | Gad et al. |
| 6,620,847 B2 | 9/2003 | Konfino et al. |
| 6,800,285 B2 | 10/2004 | Rodriguez et al. |
| 6,800,287 B2 | 10/2004 | Gad et al. |
| 6,844,314 B2 | 1/2005 | Eisenbach-Schwartz et al. |
| 6,939,539 B2 | 9/2005 | Konfino et al. |
| 7,022,663 B2 | 4/2006 | Gilbert et al. |
| 7,033,582 B2 | 4/2006 | Yong et al. |
| 7,074,580 B2 | 7/2006 | Gad et al. |
| 2001/0055568 A1 | 12/2001 | Gilbert et al. |
| 2002/0037848 A1 | 3/2002 | Einsenbach-Schartz et al. |
| 2002/0055466 A1 | 5/2002 | Aharoni et al. |
| 2002/0077278 A1 | 6/2002 | Yong et al. |
| 2002/0107388 A1 | 8/2002 | Vandenbark |

(Continued)

FOREIGN PATENT DOCUMENTS

DE 3930733 3/1991

(Continued)

OTHER PUBLICATIONS

Tisch, R et al. Proc. Nat. Acad. Sci. (USA). 1994. 91:437-438.*

(Continued)

*Primary Examiner*—Christina Chan
*Assistant Examiner*—F. Pierre VanderVegt
(74) *Attorney, Agent, or Firm*—John P. White; Cooper & Dunham LLP

(57) ABSTRACT

The present invention provides heteropolymer compositions and peptide compositions, and methods of making and using therapeutic compositions comprising amino acid heteropolymers for treatment of a subject for an autoimmune or an inflammatory disease, the heteropolymer compositions made by solid state synthesis. The invention also provides kits for assaying binding of a composition to a water-soluble MHC protein.

5 Claims, 13 Drawing Sheets

U.S. PATENT DOCUMENTS

| | | |
|---|---|---|
| 2003/0170729 A1 | 9/2003 | Klinger |
| 2004/0006022 A1 | 1/2004 | Strominger et al. |
| 2005/0019322 A1 | 1/2005 | Rodriguez et al. |
| 2005/0170004 A1 | 8/2005 | Rosenberger |
| 2005/0171286 A1 | 8/2005 | Kinfino et al. |
| 2005/0256046 A1 | 11/2005 | Gad et al. |
| 2006/0052586 A1 | 3/2006 | Dolitzky |
| 2006/0122113 A1 | 6/2006 | Pinchasi et al. |

FOREIGN PATENT DOCUMENTS

| | | |
|---|---|---|
| EP | 0378246 | 6/1990 |
| EP | 0383620 | 8/1990 |
| EP | 0359783 | 11/1995 |
| EP | WO9533475 | 12/1995 |
| EP | 1292279 | 3/2003 |
| NZ | 254996 | 8/1996 |
| RU | 1690368 | 8/1995 |
| RU | 1469826 | 11/1995 |
| SU | 451182051 | 9/1985 |
| SU | 461664845 | 7/1991 |
| WO | WO8810120 | 12/1988 |
| WO | WO9202543 | 2/1992 |
| WO | WO9403484 | 2/1994 |
| WO | WO9426774 | 11/1994 |
| WO | WO9526980 | 10/1995 |
| WO | WO9531990 | 11/1995 |
| WO | WO9531997 | 11/1995 |
| WO | WO9830227 | 7/1998 |
| WO | WO0005249 | 2/2000 |
| WO | WO0005250 | 2/2000 |
| WO | WO0018794 | 4/2000 |
| WO | WO0020010 | 4/2000 |
| WO | WO0027417 | 5/2000 |
| WO | WO0152878 | 7/2001 |
| WO | WO0160392 | 8/2001 |
| WO | 01085797 | 11/2001 |
| WO | WO0193828 | 12/2001 |
| WO | WO0193893 | 12/2001 |
| WO | WO0197846 | 12/2001 |
| WO | 02076503 | 10/2002 |
| WO | 03048735 | 6/2003 |
| ZA | 44980214 | 9/1999 |

OTHER PUBLICATIONS

Teitelbaum, et al., "Suppression of Experimental Allergic Encephalomyelitis by a Synthetic Polypeptide", *Eur. J. Immunol.*, 1971, 1, 242-248.

Teitelbaum, et al., "Suppression of Experimental Allergic Encephalomyelitis by a Synthetic Polypeptide", *Israel J. Med. Sci.*, 1971, 7, 630-631 (Abstract).

Arnon, et al., "Suppression of Experimental Allergic Encephalomyelitis by a Synthetic Copolymer Immunological Cross Reactive with Basic Encephalitogen", *Israel J. Med. Sci.*, 1972, 8, 1759-1760.

Teitelbaum, et al., "Protection Against Experimental Allergic Encephalomyelitis", *Nature*, 1972, 240, 564-566.

Webb, et al., "Further Studies on the Suppression of Experimental Allergic Encephalomyelitis by Synthetic Copolymer", *Israel J. Med. Sci.*, 1972, 8, 656-657.

Teitelbaum, et al., "Suppression of Experimental Allergic Encephalomyelitis with Basic Polymers", *Eur. J. Immunol.*, 1973, 3, 273-279.

Webb, et al., "In Vivo and in Vitro Immunological Cross-reactions between Basic Encephalitogen and Synthetic Basic Polypeptides Capable of Suppressing Experimental Allergic Encephalomyelitis", *Eur. J. Immunol.*, 1973, 3, 279-286.

Teitelbaum, et al., "Dose-response Studies on Experimental Allergic Encephalomyelitis Suppression by COP-1", *Israel J. Med. Sci.*, 1974, 10(9), 1172-1173.

U.S. Appl. No. 09/359,099, filed Jul. 22, 1999, Strominger et al.

U.S. Appl. No. 09/405,743, filed Sep. 24, 1999, Gad et al.

U.S. Appl. No. 09/816,989, filed Mar. 23, 2001, Gad et al.

U.S. Appl. No. 09/875,429, filed Jun. 5, 2001, Yong and Chabot.

U.S. Appl. No. 09/885,227, filed Jun. 20, 2001, Rodriquez and Ure.

Teitelbaum, et al., "Suppression of Experimental Allergic Encephalomyelitis in Rhesus Monkeys by a Synthetic Basic Copolymer", *Clin. Immunol. Immunopath.*, 1974, 3, 256-262.

Webb, et al., "Suppression of Experimental Allergic Encephalomyelitis in Rhesus Monkeys by a Synthetic Basic Copolymer", *Isr. J. Med. Sci.*, 1975, 11, 1388 (Abstract).

Webb, et al., "Molecular Requirements Involved in Suppression of EAE by Synthetic Basic Copolymers of Amino Acids", *Immunochem.*, 1976, 13, 333-337.

Abramsky, et al., "Effect of a Synthetic Polypeptide (COP-1) on Patients with Multiple Sclerosis and with Acute Disseminated Encephalomyelitis", *J. Neurol. Sci.*, 1977, 31, 433-438.

Teitelbaum, et al., "Suppression of Experimental Allergic Encephalomyelitis in Baboons by Cop 1", *Israel J. Med. Sci.*, 1977, 13, 1038 (Abstract).

Arnon, et al., "Suppression of EAE in Baboons by a Synthetic Polymer of Amino Acids", *Neurol.*, 1978, 28, 336 (Abstract).

Sela, et al., "Experimental Allergic Encephalomyelitis in" *Menarini Series on Immunopathology*, vol. 1, *First Symposium of Organ Specific Autoimmunity*, Cremona, Italy, Jun. 1977, (Miescher P.A. ed., Schwabe Co., Basel, 1978), 9-21.

Alvord, et al., "Myelin Basic Protein Treatment of Experimental Allergic Encephalomyelitis in Monkeys", *Ann. Neurol.*, 1979, 6, 469-473.

Keith, et al., "The Effect of COP 1, a Synthetic Polypeptide, on Chronic Relapsing Experimental Allergic Encephalomyelitis in Guinea Pigs" *J. Neurol. Sci.*, 1979, 42, 267-274.

Lando, et al., "Effect of Cyclophosphamide on Suppressor Cell Activity in Mice Unresponsive to EAE", *J. Immunol.*, 1979, 123, 2156-2160. (Abstract).

Lando et al., "Experimental Allergic Encephalomyelitis in Mice—Suppression and Prevention with COP-1", *Israel J. Med. Sci.*, 1979, 15, 868-896 (Abstract).

Teitelbaum, et al., "Blocking of Sensitization to Encephalitogenic Basic Proteins in Vitro by Synthetic Basic Copolymer (COP 1)" in *Cell Biology and Immunology of Leukocyte Function* (Academic Press, New York, 1979) 681-685.

Teitelbaum, "Suppression of Experimental Allergic Encephalomyelitis with a Synthetic Copolymer—Relevance to Multiple Sclerosis", in *Humoral Immunity in Neurological Diseases* (Karcher D., Lowenthal A. & Strosberg A.D., eds., Plenum Publishing Corp., 1979) 609-613.

Arnon, et al., "Desensitization of Experimental Allergic Encephalomyelitis with Synthetic Peptide Analogues" in *The Suppression of Experimental Allergic Encephalomyelitis and Multiple Sclerosis* (Academic Press, New York, 1980) 105-107.

Arnon, "A Synthetic Copolymer of Amino Acids in a Clinical Trial for MS Therapy" in *Progress in Multiple Sclerosis Research* (Bauer, Ritter, eds., Springer Verlag New York, 1980) 416-418.

Bornstein, et al., "Treatment of Multiple Sclerosis with a Synthetic Polypeptide: Preliminary Results", *Ann. Neurol.*, 1980, 8, 117 (Abstract).

Bornstein, et al., "Treatment of Multiple Sclerosis with a Synthetic Polypeptide: Preliminary Results", *Trans. Am. Neurol. Assoc.*, 1980, 105, 348-350.

McDermott, et al., "Antigen-induced Suppression of Experimental Allergic Neuritis in the Guinea Pig", *J. Neurol. Sci.*, 1980, 46, 137-143.

Arnon, "Experimental Allergic Encephalomyelitis—Susceptibility and Suppression", *Immunological Rev.*, 1981, 55, 5-30.

Bornstein et al., "Multiple Sclerosis: Trial of a Synthetic Polypeptide", *Ann. Neurol.*, 1982, 11, 317-319.

Brosnan, et al., "The Response of Normal Human Lymphocytes to Copolymer 1", *J. Neuropath. Exp. Neurol.*, 1983, 42, 356 (Abstract).

Lisak, et al., "Effect of Treatment with Copolymer 1 (Cop-1) on the in Vivo and in Vitro Manifestations of Experimental Allergic Encephalomyelitis (EAE)", *J. Neurol. Sci.*, 1983, 62, 281-293.

Bornstein, et al., "Clinical Trials of Copolymer 1 in Multiple Sclerosis", *Ann. N.Y. Acad. Sci. (USA)*, 1984, 366-372.
Bornstein, et al., "Clinical Trials of a Synthetic Polypeptide (Copolymer 1) for the Treatment of Multiple Sclerosis" in Gonsett et al., *Immunological and Clinical Aspects of Multiple Sclerosis* (MTP Press, The Hague, 1984) 144-150.
Brosnan, et al., "Copolymer 1: Effect on Normal Human Lymphocytes", *Ann. N.Y. Acad. Sci. (USA)*, 1984, 436, 498-499.
Bornstein, et al., "Multiple Sclerosis: Clinical Trials of a Synthetic Polypeptide, Copolymer 1", *Neurol.*, 1985, 35 (Suppl. 1), 103 (Abstract).
Brosnan, et al., "Immunogenic Potentials of Copolymer 1 in Normal Human Lymphocytes", *Neurol.*, 1985, 35, 1754-1759.
Burns, et al., "Human Cellular Immune Response in Vitro to Copolymer 1 and Myelin Basic Protein (MBP)", *Neurol.*, 1985, 35 (Suppl. 1), 170 (Abstract).
Teitelbaum, et al., "Monoclonal Antibodies to Myelin Basic Protein Cross React with Synthetic EAE-suppressive Copolymer, COP 1" in *Proc. 7th Eur. Immunol. Mtg.*, Jerusalem, Sep. 8-13, 1985 (Abstract).
Thompson, "MCQ Tutor: Medical Immunology Multiple Choice Questions", *Immunol. Today*, 1985, 6(4), 141.
Burns, et al., "Human Cellular Immune Response to Copolymer 1 and Myelin Basic Protein", *Neurol.*, 1986, 36, 92-94.
Bornstein, "Cop 1 May be Beneficial for Patients with Exacerbating—remitting Form of Multiple Sclerosis", *Adv. Ther. (USA)*, 1987, 4, 206 (Abstract).
Bornstein, et al., "A Pilot Trial of Cop 1 in Exacerbating-remitting Multiple Sclerosis", *New Eng. J. Med.*, 1987, 317(7), 408-414.
Rolak, "Copolymer-I Therapy for Multiple Sclerosis", *Clin. Neuropharmacology*, 1987, 10(5), 389-396.
Winer, "COP 1 Therapy for Multiple Sclerosis", *New Eng. J. Med.*, 1987, 317(7), 442-444.
Arnon, et al., "Suppression of Demyelinating Disease by Synthetic Copolymers", in *A Multidisciplinary Approach to Myelin Disease* (G. Serlupi Crescenzi, ed., Plenum Publishing Corp., 1988) 243-250.
Baumhefner, et al., "Copolymer 1 as Therapy for Multiple Sclerosis: The Cons", *Neurol.*, 1988, 38(Suppl. 2), 69-71.
Bornstein, et al., "Clinical Experience with COP-1 in Multiple Sclerosis", *Neurol.*, 1988, 38(Suppl. 2), 66-69.
Teitelbaum, et al., "Specific Inhibition of the T-cell Response to Myelin Basic Protein by the Synthetic Copolymer Cop 1", *Proc. Natl. Acad. Sci. USA*, 1988, 85, 9724-9728.
Arnon, et al., "Suppression of Experimental Allergic Encephalomyelitis by Cop-1—Relevance to Multiple Sclerosis", *Israel J. Med. Sci.*, 1989, 25, 686-689.
Bornstein, et al., "Pilot Trial of COP-1 in Chronic Progressive Multiple Sclerosis: Preliminary Report", from *The International Multiple Sclerosis Conference: An Update on Multiple Sclerosis*, Roma (Italy), Sep. 15-17, 1988, in *Elsevier Science Publisher*, 1989, 225-232.
Teitelbaum, et al., "Clinical Trial of Copolymer 1 in Multiple Sclerosis" *J. Israel Med. Assoc.*, 1989, CXVI(9), 453-456.
Bornstein, et al., "Clinical Trials of Cop 1 in Multiple Sclerosis" in *Handbook of Multiple Sclerosis* (S.D. Cook Marcel Rekker, ed., 1990) 469-480.
Carter, et al., "Newer Drug Therapies for Multiple Sclerosis", *Drug Therapy*, 1990, 31-32, 37-39, 42-43.
Grgacic, et al., "Cell-mediated Immune Response to Copolymer 1 in Multiple Sclerosis Measured by the Macrophage Procoagulant Activity Assay", *Int. Immunol.*, 1990, 2(8), 713-718.
Kay, et al., "The Mechanism of Action of FK 506", *Transplantation Proceedings*, 1990, 22(1, Suppl. 1), 96-99.
Lee, et al., "Peptide and Protein Drug Delivery" in *Advances in Parenteral Sciences* (Vincent H.L. Lee, ed., Marcel Dekker, Inc., 1990) 691-695.
Myers, et al., "The Peculiar Difficulties of Therapeutic Trials for Multiple Sclerosis", *Neurologic Clinics*, 1990, 8(1), 119-141.
Sela, et al., "Suppressive Activity of COP-1 in EAE and its Relevance to Multiple Sclerosis", *Bull. Inst. Pasteur*, 1990, 88, 303-314.
Starzl, *Transplantation Proceedings*, 1990, 22 (1, Suppl. 1), 5.

Wender, "Copolymer 1 (COP-1) in the Treatment of Multiple Sclerosis (letter)", *Neur. Neurochir. Pol.*, 1990, 24, 113.
Bornstein, et al., "A Placebo-controlled, Double-blind, Randomized Two-center, Pilot Trial of Cop 1 in Chronic Progressive Multiple Sclerosis", *Neurol.*, 1991, 41, 533-539.
Burns, et al., "Failure of Copolymer 1 to Inhibit the Human T-cell Response to Myelin Basic Protein", *Neurol.*, 1991, 41, 1317-1319.
Clinical Trial Protocol No. 9001, Teva Pharmaceutical Industries, Ltd., first patient enrolled Oct. 23, 1991.
Ferrara, et al., "Graft-Versus-Host Disease", *New Eng. J. Med.*, 1991, 324, 667-674.
Meiner, "COP-1 Multicenter Clinical Trial in Exacerbating-remitting Multiple-Sclerosis: One Year Follow-up", *J. Neurol.*, 1991(Suppl. 1) (Abstract).
Rothbard, et al., "Interactions Between Immunogenic Peptides and MHC Proteins", *Ann. Rev. Immunol.*, 1991, 9, 527-565.
Salvetti, et al., "Myelin Basic Protein T Cell Epitopes in Patients with Multiple Sclerosis", *Department of Neurological Sciences, University of Rome, La Sapienza* 1991, 72 (Abstract).
Teitelbaum, et al., "Cross-reactions and Specificities of Monoclonal Antibodies Against Myelin Basic Protein and Against the Synthetic Copolymer 1", *Proc. Natl. Acad. Sci. (USA)*, 1991, 88, 9528-9532.
Van den Bogaerde, et al., "Induction of Long-Term Survival of Hamster Heart Xenografts in Rats", *Transplantation*, 1991, 52, 15-20.
Bornstein et al., "Treatment of Multiple Sclerosis with Copolymer 1" in *Treatment of Multiple Sclerosis: Trial Design, Results and Future Perspectives* (Rudick R.A. & Goodkin D.E., eds., Springer Verlag, London, 1992, 173-198.
Johnson, "Clinical Studies in Copolymer 1 Therapy for Exacerbating-remitting Multiple Sclerosis", in *Congress for Advances in the Understanding and Treatment of Multiple Sclerosis*, Boston (USA), Oct. 28-29, 1992.
Milo, et al., "Inhibition of Myelin Basic Protein-specific Human T-cell Lines by COP-1", *Israel J. Med. Sci.*, 1992, 28, 486 (Abstract).
Racke, et al., "Copolymer-1-induced Inhibition of Antigen-specific T Cell Activation: Interference with Antigen Presentation", *J. Neuroimmunol.*, 1992, 37, 75-84.
Teitelbaum, et al., "Synthetic Copolymer 1 Inhibits Human T-cell Lines Specific for Myelin Basic Protein", *Proc. Natl. Acad. Sci. (USA)*, 1992, 89, 137-141.
Weinshenker, et al., "Natural History and Treatment of Multiple Sclerosis", *Current Opinion in Neurol. and Neurosurgery*, 1992, 5, 203-211.
Aharoni, et al., "T Suppressor Hybridomas and Interleukin-2-Dependent Lines Induced by Copolymer 1 or by Spinal Cord Homogenate Down-Regulate Experimental Allergic Encephalomyelitis", *Eur. J. Immunol.*, 1993, 23, 17-25.
Arnon, et al., "Immunomodulation of Experimental Allergic Encephalomyelitis", *Israel J. Med. Sci.*, 1993, 29, 175-181.
Arnon, et al., "On the Existence of Suppressor Cells", *Int. Arch. Allergy Immunol.*, 1993, 100, 2-7.
Clinical Trial Protocol No. 9002, Lemmon Co. and Teva Pharmaceutical Industries, Ltd., first patient enrolled Jun. 17, 1993.
Francis, "The Current Therapy of Multiple Sclerosis", *J. Clin. Pharmacy and Therapeutics*, 1993, 18, 77-84.
Keleman, et al., "Graft-versus-Host Disease in Bone Marrow Transplantation: Experimental, Laboratory, and Clinical Contributions of the Last Few Years", *Int. Arch. Allergy Immunol.*, 1993, 102, 309-320.
Gurevich, "Study of the MHC-competition Between BP and Cop 1 Using Human Cytotoxic T-cell Clones", *Israel J. Med. Sci.*, 1993 (Abstract).
Meiner et al., "The Israeli COP-1 Multicancer Clinical Trial in Exacerbating-remitting Multiple Sclerosis—Two year Follow-up", in *9th Congress of the European Committee for Treatment and Research in Multiple Sclerosis*, Florence (Italy), Oct.-Nov. 1993, 48 (Abstract).
Milo, et al., "Copolymer-1 (COP-1) Regulates Class II MHC Expression and Cytokine Synthesis in the THP-1 Monocyte-Macrophage Cell Line" in *The IBC Conference on Multiple Sclerosis*, San Diego (USA), Dec. 10, 1993 (Abstract).

Sela, "Polymeric Drugs as Immunomodulatory Vaccines Against Multiple Sclerosis", *Makromol. Chem. Macromol. Symp.*, 1993, 70/71, 147-155.

Arnon, et al., "Immunospecific Drug Design—Prospects for Treatment of Autoimmune Disease", *Therapeutic Immunol.*, 1994, 1, 65-70.

Bansil, et al., "Multiple Sclerosis: Pathogenesis and Treatment", *Seminars in Neurol.*, Jun. 1994, 14(2), 146-153.

The COP-1 Multicenter Clinical and Research Group Study, "COP-1 Multicenter Trial in Relapsing Remitting Multiple Sclerosis: 3 Year Follow Up", *Abstracts of Symposia and Free Communication*, Barcelona (Spain), Jun. 25-29, 1994, 241 (Suppl. 1), 6.

Cotton, "Options for Multiple Sclerosis Therapy", *J.A.M.A. Medical News & Perspectives*, 1994, 272(18), 1393.

Dorling, et al., "Prospects for Xenografting", *Curr. Opinions Immunol.*, 1994, 6, 765-769.

Fridkis-Hareli, et al., "Copolymer 1 Displaces MBP, PLP and MOG, but Can Not be Displaced by these Antigens from the MHC Class II Binding Site", *Department of Chemical Immunology, The Weizmann Institute of Science*, 1994.

Fridkis-Hareli, et al., "Direct Binding of Myelin Basic Protein and Synthetic Copolymer 1 to Class II Major Histocompatibility Complex Molecules on Living Antigen-Presenting Cells—Specificity and Promiscuity", *Proc. Natl. Acad. Sci. USA*, 1994, 91, 4872-4876.

Fridkis-Hareli, et al., "Specific and Promiscuous Binding of Synthetic Copolymer 1 to Class II Major Histocompatibility Complex Molecules on Living Antigen Presenting Cells", *Israeli Biochem. Soc.*, 1994, 21-22 (Abstract).

Fridkis-Hareli, et al., "Synthetic Copolymer 1 Inhibits the Binding of MBP, PLP and MOG Peptides to Class II Major Histocompatibility Complex Molecules on Antigen Presenting Cells" in *Neurochem Mtg.*, Aug. 14-19, 1994.

Fridkis-Hareli, et al., "Synthetic Copolymer 1 Inhibits the Binding of MBP, PLP and MOG Peptides to Class II Major Histocompatibility Complex Molecules on Antigen- Presenting Cells", *J. Neurochem.*, 1994, 63(Suppl. I), 561.

Fridkis-Hareli, et al., "Synthetic Copolymer 1 and Myelin Basic Protein do not Require Processing Prior to Binding to Class II Major Histocompatibility Complex Molecules on Living Antigen Presenting Cells", *Department of Chemical Immunology, The Weizmann Institute of Science*, Rehovot, Israel, 1994.

Fridkis-Hareli, et al., "Synthetic Copolymer 1 and Myelin Basic Protein Do Not Require Processing Prior to Binding to Class II Major Histocompatibility Complex Molecules on Living Antigen-Presenting Cells", *Cell. Immunol.*, 1995, 163, 229-236.

Fridkis-Hareli, et al., "Synthetic Copolymer 1 and Myelin Basic Protein Do Not Undergo Processing Prior to the Binding to Class II Major Histocompatibility Complex Molecules on Antigen Presenting Cells", *Israeli Immunol. Soc.*, May 3-4, 1994 (Abstract).

Jacobs, et al., "Advances in Specific Therapy for Multiple Sclerosis", *Neurol.*, 1994, 7, 250-254.

Johnson, "Experimental Therapy of Relapsing-Remitting Multiple Sclerosis with Copolymer-1", *Ann. Neurol.*, 1994, 36(Suppl.), 115-117.

Kott, et al., "COP-1 Increases Suppressor Cells Number in Multiple Sclerosis", *Israel Neurological Assoc.*, Dec. 19-20, 1994, Herzliya (Israel), 17.

Mengle-Gaw, "The Major Histocompatibility Complex (MHC)", in *Encycl. Molecular Bio.* (Oxford Blackwell Science Ltd, 1994) 602-606.

Milo, et al., "Additive Effects of COP-1 and IFN-Beta on Immune Responses to Myelin Basic Protein", *Neurol.*, 1994, 44(Suppl. 2), A212.

Milo et al., "Additive Effect of Copolymer-1 and Interferon-B on the Immune Response to Myelin Basic Protein", *Assaf Harofeh Medical Center, Sackler School of Medicine, Tel-Aviv University of Maryland School of Medicine*, 1994, 22.

Milo, et al., "Copolymer-1 and Interferon-β Additively Suppress the Immune Response to Myelin Basic Protein by Inhibiting Antigen Presentation", *J. Neuroimmunol.*, 1994, 54, 183 (Abstract).

Nightingale, et al., "Access to Investigational Drugs for Treatment Purposes", *Am. Family Physician*, 1994, 50(4), 845-847.

Tisch et al., "Antigen-specific immunotherapy: Is it a Real Possibility to Combat T-Cell-Mediated autoimmunity?" *Proc. Natl. Acad. Sci. U.S.A.*, 1994, 91, 437-438.

Schlegel, et al., "Prevention of Graft-Versus-Host Disease by Peptides Binding to Class II Major Histocompatibility Complex Molecules", *Blood*, 1994, 84(8), 2802-2810.

Stark, "Expanded Clinical Trials of Treatments for Multiple Sclerosis (MS): Copolymer 1 (COP-1) Treatment Investigational New Drug (IND) Program", *Ann. Neurol.*, 1994, 36, 114-115.

Teitelbaum, et al., "Immunological Parameters in a Multicenter Clinical Trial of COP1 in Multiple Sclerosis (MS): A 2-year Follow-up", *Neurol.*, 1994, 44(Suppl. 2), A358.

Milo, et al., "Additive Effects of Copolymer-1 and Interferon β-1b on the Immune Response to Myelin Basci Protein", *J. Neuroimmunol.*, 1995, 61, 185-193.

O'Connor, et al., "Powders" in *The Science and Practice of Pharmacy*, Remington, 1995, 2, 1598-1614.

Porter, "Coating of Pharmaceutical Dosage Forms," in *The Science and Practice of Pharmacy*, Remington, 1995, 2, 1650-1659.

Reilly, Jr., W.J., "Pharmaceutical Necessities" in *The Science and Practice of Pharmacy*, Remington 1995, 2, 1380-1416.

Schlegel, et al., "Inhibition of Allorecognition and Prevention of Graft-vs-host Disease (GVHD) by GLAT, a Synthetic Polymer with Promiscuous Binding to Murine and Human MHC Class II Molecules", in *Am. Soc. Hematology, 37th Annual Meeting*, Seattle, WA (USA), Dec. 1-5, 1995, 224a (Abstract).

Ben-Nun, e al., "The Autoimmune Reactivity to Myelin Oligodendrocyte Glycoprotein (MOG)in Multiple Sclerosis is Potentially Pathogenic: Effect of Copolymer 1 on MOG-induced Disease", *J. Neurol.*, 1996, 243(Suppl. 1), S14-S22.

Johnson, Management of Relapsing/Remitting Multiple Sclerosis with Copolymer 1 (Copaxone)", *Chemical Abstracts*, 1996, 125, 291993b.

Sykes, "Immunobiology of Transplantation", *Faseb J.*, 1996, 10, 721-730.

Teitelbaum, et al., "Copolymer 1 Inhibits Chronic Relapsing Experimental Allergic Encephalomyelitis Induced by Proteolipid Protein (PLP) Peptides in Mice and Interferes with PLP-specific T Cell Responses", *J. Neuroimmunol.*, 1996, 64, 209-217.

Aharoni, et al., "Studies on the Mechanism and Specificity of the Effect of the Synthetic Random Copolymer GLAT on Graft-versus-Host Disease", *Immunol. Letters*, 1997, 58, 79-87.

Puri et al., "Modulation of the Immune Response in Multiple Sclerosis", *J. Immunol.*, 1997, 2471-2476.

Tarcic et al., "Copolymer 1 (Copaxone) from an Idea to a Drug for Treatment of Multiple Sclerosis" Database HCAPLUS on STN, Israel: An 1997:333270. Kim, Handasa Kim, 1997, 281(14), 16-18 (Abstract).

Teitelbaum, et al., "Copolymer 1 from the Laboratory to FDA", *Israel J. Med. Sci.*, 1997, 33, 280-284.

Fridkis-Hareli, et al., "Promiscuous Binding of Synthetic Copolymer 1 to Purified HLA-DR Molecules", *J. Immunol.*, 1998, 160, 4386-4397.

Durelli, "Immunotherapeutics of Multiple Sclerosis", *Instituto di Clinica delle Malattie del Sistema Nervoso Universita di Torino*, 467-475.

Kropshofer et al., "Self-Peptides from Four HLA-DR Alleles Share Hydrophobic Anchor Residues Near the $NH_2$-Terminal Including Proline as a Stop Signal for Trimming", *J. Immunol.*, 1993, 151:4732-4742.

U.S. Appl. No. 09/487,793, filed Jan. 20, 2000.

U.S. Appl. No. 09/620,216, filed Jul. 20, 2002.

U.S. Appl. No. 09/765,301.

U.S. Appl. No. 09/765,644.

Fridkis-Hareli et al., "Synthetic Peptides that Inhibit Binding of the Collagen Type II 261-273 Epitope to Rheumatoid Arthritis-Associated HLA-DR1 and DR4 Molecules and Collagen-Specific T-cell Responses", Database HCAPLUS on STN, Department of Clinical Immunology, Aarhus University Hospital, Aarhus, Denmark, HCAPLUS AN: 2000:455053, Human Immunology, 2000, 61(7): 640-650 (Abstract).

Henry, Celia M., "Special Delivery", *Chem. and Eng. News*, Sep. 18, 2000, 49-54.

Cazzato, et al., "Treatment of Multiple Sclerosis. The Present and the Future. Study Group on Diagnosis and Therapy of Multiple Sclerosis", Database Medline on STN, Instituto do Clinica Neurologica, Universit'a, Trieste, Italy: Medline AN: 2000060325, Recent Progressi in Medicina, Oct. 1999, 90(10): 538-544 (Abstract).

Cohen, "Fundamental Immunology", *Systemic Autoimmunity*, 4th Ed., 1999, 1083.

Fridkis-Hareli et al., "Binding of random copolymers of three amino acids to class II MHC molecules", *Intl. Immunol.*, 1999, 11(5): 635-641.

Kepsutlu et al., "Evaluation of Chitosan Used as an Excipient in Tablet Formulations", Database HCAPLUS on STN, Department of Pharmaceutical Technology, Gulhane Military Medical Academy, Ankara, 06018, Turkey, HCAPLUS AN: 1999: 590411, Acta. Pol. Pharm. 1999, 56(3): 227-235 (Abstract).

Prat, et al., "Lymphocyte Migration and Multiple Sclerosis: Relation with Disease Course and Therapy," *Ann. Neurol.*, 1999, 46: 253-256.

Fridkis-Hareli, et al., "Synthetic Amino Acid Copolymers that Bind to HLA-DR Proteins and Inhibit Type II Collagen-reactive T Cell Clones", *Proc. Natl. Acad. Sci.*, Oct. 1998, 95: 12528-12531.

Li et al., "Glatiramer acetate blocks the activation of THP-1 cells by interferon-γ", *Eur. J. Pharmacol.*, 1998, 342: 303-310.

Zisman et al., "Dichotomy between the T and the B cellepitopes of the synthetic polypeptide (T,G)-A—L", *Eur. J. Immunol.*, 1994, 24(10): 2497-2505 (Abstract).

Deeb et al., "Comparison of Freund's and Ribi adjuvants for inducing antibodies to the synthetic antigen (TG)-AL in rabbits", *J. Immunol. Methods*, 1992, 152(1):105-113 (Abstract).

Zisman et al., "Direct binding of a synthetic multichain polypeptide to Class II Major Histocompatibility Complex molecules on Antigen-Presenting Cells and stimulation of a specific T-cell line require processing of the polypeptide", *Proc. Natl. Acad. Sci. USA*, 1991, 88(21): 9732-9742 (Abstract).

Matsunaga et al., "Complementation of Class II A alleles in the immune response to (Glu-Lys-Tyr) polymers", *Yokohama Med. Bull.*, 1988, 39(1-2): 9-19 (Abstract).

De Kruyff et al., "Analysis of T Cell Responses to Poly-L (GluLys) at the Clonal Level. I. Presence of Responsive Clones in Nonresponder Mice", *Eur. J. Immunol.*, 1987, 17 (8): 1115-1120 (Abstract).

Lai et al., "Complementation of Class II A alleles in the immune response to (GluLysTyr) polymers", *Exp. Clin. Immunogenet.*, 1986, 3(1): 38-48 (Abstract).

Lai et al., "Monoclonal T cell response to two epitopes on a single immunogen controlled by two distinct genes", *J. Immunol.*, 1986, 136(10): 3799-3804 (Abstract).

Trannoy et al., "Epitope-specific regulation of the T cell repertoire: carrier recognition in association with I-E or I-A does not influence the restriction of hapten-specific T cells", *Eur. J. Immunol.*, 1985, 15(12): 1215-1221 (Abstract).

Falo et al., "Analysis of antigen presentation by metabolically inactive accessory cells and their isolated membranes", Proc. Natl. Acad. Sci. USA, 1985 82 (19): 6647-6651 (Abstract).

Babu et al., "Ir gene control of T and B Cell Responses to Determinants in (Glu Lys Ala) Terpolymer", J. Immunogenet., 1984, 11(3-4): 251-254.

Babu et al., "Reevaluation of response patterns of nonresponder mice to GLPhe polymers", *Immunogen.*, 1983, 18(1): 97-100 (Abstract).

Herzenberg et al., "Lack of immune response gene control for induction of epitope-specific suppression by TGAL antigen", *Nature*, 1982, 295: 329-331 (Abstract).

Baxevanis et al., "Genetic Control of T-Cell Proliferative Responses to Poly (Glu$^{40}$Ala$^{60}$) and Poly (Glu$^{52}$Lys$^{34}$Tyr$^{15}$): Subregion-Specific Inhibition of the Responses with Monoclonal Ia Antibodies", *Immunogenetics*, 1980, 11: 617-628.

Maurer et al., "Interpretations of immune responses of mice to poly(Glu60Lys40), its modified derivatives, and the terpolymers poly (Glu55Lys37Leu8) and poly (Glu56Lys37Ser7)", *Clin. Immunol. Immunopathol.*, 1980, 15(3): 344-356 (Abstract).

Ju et al., "Idiotypic analysis of antibodies against the terpolymer L-glutamic acid 60-L-alanine30-L-tyrosine10 (GAT). IV. Induction of CGAT idiotype following immunization with various synthetic polymers containing glutamic acid and tyrosine", *Eur. J. Immunol.*, 1979, 9(7): 553-560 (Abstract).

Schwartz et al., "Gene complementation in the T lymphocyte proliferative response to poly (Glu57Lys38Tyr5): Evidence for effects of polymer handling and gene dosage", *J. Immunol.*, 1979, 123(1): 272-278 (Abstract).

Aharoni, et al., "Copolymer 1 induces T cells of the T helper type 2 that crossreact with myelin basic protein and suppress experimental autoimmune encephalomyelitis", *Proc. Natl. Acad. Sci. USA*, 1997, 94, 10821-10826.

Aharoni, et al., "Cop 1 Specific Supporessor Cells Inhibit Experimental Allergic Encephalomyelitis Induced by Either Mouse Spinal Cord Homogenate or Proteolipid Protein Peptide 139-151", *Neurology*, 1997 vol. 48, No. 3, A422.

Aharoni, et al., "Bystander suppression of experimental autoimmune encephalomyelitis by T cell lines and clones of the Th2 type induced by copolymer 1", *Journal of Neuroimmunology*, 1998, 98, 135-146.

Asakura et al., "A unique population of circulating autoantibodies promotes central nervous system remyelination", *Multiple Sclerosis*, 1998, 4, 217-221.

Asakura et al., "Targeting of IgMk Antibodies to Oligodendrocytes Promotes CNS Remyelination", *The Journal of Neuroscience*, 1998, 18(19), 1700-1108.

Batchelor, et al., *Lancet*, 1980 1(8178):1107-9.

Bieber, et al., "Antibody-mediated remyelination: relevance to multiple sclerosis", *Multiple Sclerosis*, 2000, 6(2), S1-S5.

Bieber, et al., "Humoral autoimmunity as a mediator of CNS repair", *A Trends Guide to Neurodegenerative Disease and Repair/ Review*, 2001, 24(11), S39-S44.

Bodanszky, M., "Principles of Peptide Synthesis," Springer-Verlag, Berlin, Heidelberg, New York, Tokyo, 1984, 118-229.

Bornstein, Clinical Experience: Hopeful Prospects In Multiple Sclerosis, *Hospital Practice*, 1992, vol. 27, No. 5, pp. 135-158.

Duda, et al., "Human and Murine CD4 T Cell Reactivity to a Complex Antigen: Recognition of the Synthetic Random Polypeptide Glatiramer Acetate", *The Journal of Immunology*, 2000, 165, 7300-7307.

Fatma, et al., *Swiss Med. Wkly*, 2003, 133:541-543.

Giuseppina, et al., *The Journal of Clinical Investigation*, Apr. 2003, vol. 111, No. 8, 1171-80.

Harrison and Hafler, "Antigen-Specific Therapy for Autoimmune Disease", *Current Opin. Immunol.*, 2000, 12(6): 704-711.

Johnson, et al. "Copolymer 1 reduces relapse rate and improves disability in relapsing-remitting multiple sclerosis: results of a phase III multicenter, double-blind placebo-controlled trial. The Copolymer 1 Multiple Sclerosis Study Group", *Neurology*, 45(7), 1268 (abstract).

Kobayashi, et al., *Clinical Exp. Immunology*, Jun. 1990, 80(3):400-3.

Korezyn, et al., "Safety profile Of copolymer 1: Analysis Of Cumulative Experience in the United States and Israel", *J. Neurol*, 1996, vol. 243 (Suppl. 1), S23-S26.

Lombardi, et al., *J. Invest. Dermatol.*, Jul. 1999 113(1):107-10.

Lovell, K. and Jones, M., "CNS Infections, Spongiform Encephalopathy and Demyelinating Diseases," Karol Mareinkowski U. Med. Sci., Dept. Pathol., Poland, last updated on Apr. 20, 2003, <URL:http://ampat.amu.edu.pl/guzyuno/CNS_INFE.HTM>.

Lymberi, et al., *Arch. Hellen. Med.*, 16(4), Jul.-Aug. 1999, 337-351.

McGavern, et al., "Do Antibodies Stimulate Myelin Repair in Multiple Sclerosis?", *The Neuroscientist*, 1999, 5(1), 19-28.

Merck Manual of Diagnosis and Therapy, *Merck Research Laboratories*, Whitehouse Section, N.J., 17th Ed., 1999, 1300-1303, 1312-1317.

Pavelko, et al., "Acceleration in the Rate of CNS Remyelination in Lysolecithin-Induced Demyelination", *The Journal of Neuroscience*, 1998 18(7), 2498-2505.

Pender, et al., Internal Med. Journal, 2002, 32: 554-563.

Pharmacia Biotech Directory, 1996, pp. 340-341.

Physician's Desk Reference, 2000, Medical Economics Co. Inc., Montvale, NJ, 3115.

Racadot, et al., "Treatment of Multiple Sclerosis With Anti-CD4 Monoclonal Antibody", *J. of Autoimmunity*, 1993, vol. 6, pp. 771-786.

Rodriguez, et al., "Immunoglobulins Reactive With Myelin Basic Protein Promote CNS Remyelination", *Neurology*, 1996, vol. 46, pp. 538-545.

Rodriguez, et al., Neurological Therapeutics, 1998, *15*(3): 245-250.

Sela, M., et al., "Synthetic Approaches to Vaccines for Infectious and Autoimmune Diseases", *Vaccine*, 1992, vol. 10, Issue 14, 991-999.

Sridama, et al., *Arch Intern Med.*, 1987, 147:229-231.

Teva, et al., "Copolymer-1 Glatiramer Acetate Copaxone Agent for Multiple Sclerosis". *Drugs of the Future*, 1998, vol. 23, No. 2, 213-214.

Ure, et al., "Polyreactive Antibodies To Glatiramer Acetate Promote Myelin Repair In Murine Model Of Demyelinating Diseas", *FASEB Journal*, 2002, vol. 16, pp. 1260-1262.

U.S. Appl. No. 10543764, filed Jul. 18, 2005, Aharoni et al.

U.S. Appl. No. 10547463, filed Aug. 30, 2005, Pinchasi et al.

Vandenbark, et al., "Specificity Of T Lymphocyte Lines For Peptide Of Myelin Basic Protein", *The J. Of Immunology*, 1985, vol. 135, pp. 229-233.

Van Noort, et al., *International Review of Cytology*, 1996, 178: 127-205.

Wan, et al., *Human Immunology*, 2002, Apr. 63(4):301-10.

Warrington, et al., "Immunoglobulin-mediated CNS repair", *J. Allergy Clin. Immunol.*, 2001, S121-S125.

Warrington, et al., "Human monoclonal antibodies reactive to oligodenrocytes promote remyelination in a model of multiple sclerosis", *Neurobiology*, 2000, 97(12), 6820-6825.

Webster's II New Riverside University Dictionary, definition of "preventing", The Riverside Publishing Co., 1984, p. 933.

Weilbach, et al., "Disease Modifying Treatments For Multiple Sclerosis: What Is On The Horizon?" *CNS Drugs*, 1999, vol. 11, No. 2, pp. 133-167.

Wiesemann, et al., "Glatiramer Acetate (GA) induces IL-13/IL-5 secretion in naïve T cells", *Journal of Neuroimmunology*, 2001, 119, 137-144.

Zhang, et al., "Murine Monoclonal Anti-Myelin Basic Protein (MBP) Antibodies Inhibit Proliferation And Cytotoxicity Of MBP-specific human T cells clones", *J. of Neuroimmunology*, 1989, vol. 24, pp. 87-94.

"About Copaxone", Internet Article URL: http://www.mswatch.com/therapy/section.aspx?SectionId=789eabf5-3a07-4dff-a7ee-0d4ad138a6d.

URL: http://ntri.tamuk.edu/immunology/autoimmunity.html.

U.S. Appl. No. 10556454, filed Nov. 17, 2005, Vollmer.

U.S. Appl. No. 10577588, filed Apr. 27, 2006, Rosenberger et al.

U.S. Appl. No. 11228850, filed Sep. 14, 2005, Schwartz.

U.S. Appl. No. 11336251, filed Jan. 20, 2006, Dolitzky.

U.S. Appl. No. 11373794, filed Mar. 9, 2006, Pinchasi.

\* cited by examiner

TREATMENT OF AUTOIMMUNE CONDITIONS WITH COPOLYMER 1 AND RELATED COPOLYMERS

RELATED APPLICATIONS

The present application is a continuation of PCT/US99/16747, filed Jul. 23, 1999, which claims the benefit of provisional applications 60/093,859 filed Jul. 23, 1998, 60/101,825, filed Sep. 25, 1998, 60/102,960, filed Oct. 2, 1998, 60/106,350, filed Oct. 30, 1998, and 60/108,184, filed Nov. 12, 1998, all of which are incorporated by reference herein.

GOVERNMENT FUNDING

This invention was made in part with government support under grant CA47554 awarded by the National Institutes of Health. The government has certain rights in the invention.

INTRODUCTION

The present invention provides compositions and methods for treating autoimmune diseases using therapeutically effective amounts of a polypeptide related to Copolymer 1. Copolymer 1 is a heterogeneous mixture of synthetic random linear copolymers of tyrosine, alanine, glutamic acid and lysine and, in appropriate therapeutic amounts and average molecular sizes, is used to treat multiple sclerosis. When such mixtures of synthetic random linear copolymers consist essentially of the three of the four amino acids found in Copolymer 1, they are referred to as Terpolymers. The present invention relates in part to Terpolymers. Preferably, the Terpolymers are composed of tyrosine, alanine and lysine, or of glutamic acid, tyrosine and lysine, or of glutamic acid, alanine and lysine. Surprisingly, the Terpolymers have efficacy for treating a variety of auto-immune diseases and bind to Class II major histocompatibility complex (MHC) molecules as well as to antigen presenting cells.

BACKGROUND OF THE INVENTION

Autoimmune diseases occur when an organism's immune system fails to recognize some of the organism's own tissues as "self" and attacks them as "foreign." Normally, self-tolerance is developed early by developmental events within the immune system that prevent the organism's own T cells and B cells from reacting with the organism's own tissues. MHC cell surface proteins help regulate these early immune responses by binding to and presenting processed peptides to T cells.

This self-tolerance process breaks down when autoimmune diseases develop. Now the organism's own tissues and proteins are recognized as "autoantigens" and are attacked by the organism's immune system. For example, multiple sclerosis is believed to be an autoimmune disease occurring when the immune system attacks the myelin sheath, whose function is to insulate and protect nerves. It is a progressive disease characterized by demyelination, followed by neuronal and motor function loss. Rheumatoid arthritis ("RA") is also believed to be an autoimmune disease which involves chronic inflammation of the synovial joints and infiltration by activated T cells, macrophages and plasma cells, leading to a progressive destruction of the articular cartilage. It is the most severe form of joint disease. The nature of the autoantigen(s) attacked in rheumatoid arthritis is poorly understood, although collagen type II is a candidate.

A tendency to develop multiple sclerosis and rheumatoid arthritis is inherited—these diseases occur more frequently in individuals carrying one or more characteristic MHC class II alleles. For example, inherited susceptibility for rheumatoid arthritis is strongly associated with the MHC class II DRB1 *0401, DRB 1 *0404, or DRB 1*0405 or the DRB1*0101 alleles. The histocompatibility locus antigens (HLA) are found on the surface of cells and help determine the individuality of tissues from different persons. Genes for histocompatibility locus antigens are located in the same region of chromosome 6 as the major histocompatibility complex (MHC). The MHC region expresses a number of distinctive classes of molecules in various cells of the body, the genes being, in order of sequence along the chromosome, the Class I, II and III MHC genes. The Class I genes consist of HLA genes, which are further subdivided into A, B and C subregions. The Class II genes are subdivided into the DR, DQ and DP subregions. The MHC-DR molecules are the best known; these occur on the surfaces of antigen presenting cells such as macrophages, dendritic cells of lymphoid tissue and epidermal cells. The Class III MHC products are expressed in various components of the complement system, as well as in some non-immune related cells.

A number of therapeutic agents have been developed to treat autoimmune diseases, including steroidal and non-steroidal anti-inflammatory drugs, for example, methotrexate; various interferons; and certain inhibitors of prostaglandin synthesis. However, these agents can be toxic when used for more than short periods of time or cause undesirable side effects. Other therapeutic agents bind to and/or inhibit the inflammatory activity of tumor necrosis factor (TNF), for example, anti-TNF specific antibodies or antibody fragments, or a soluble form of the TNF receptor. These agents target a protein on the surface of a T cell and generally prevent interaction with an antigen presenting cell (APC). However, therapeutic compositions containing natural folded proteins are often difficult to produce, formulate, store, and deliver. Moreover, the innate heterogeneity of the immune system can limit the effectiveness of drugs and complicate long-term treatment of autoimmune diseases.

Thus in order to effectively treat autoimmune diseases and other immune conditions, new drugs are needed that do not have the side effects of the present therapeutic agents and which adequately address to the innate heterogeneity of the immune system.

REFERENCES

Aharoni, et al., 58 Immunology Letters 79 (1997).
Allison, in IMMUNOSUPPRESSION AND ANTI-INFLAMMATORY DRUGS, ANNALS OF THE NEW YORK ACADEMY OF SCIENCE 696:xi (1993).
Ben-Nun A et al., 243 J NEUROL (Suppl 1) S14-S22 (1996).
Dorling et al., 6 CUR. OPINIONS IMMUNOL. 765 (1994).
Ferrara et al., 324 NEW ENGLAND J. OF MEDICINE 667 (1991).
Fridkis-Hareli, et al., 63 J. NEUROCHEM. 63 (Suppl. 1) S61 (1994).
Fridkis-Hareli, et al., 163 CELL. IMMUNOL. 229. (1995).
Fridkis-Hareli, et al., 160 J. IMMUNOL. 4386 (1998).
Johnson, 1 NEUROLOGY 65-70 (1995).
Kay et al., 22 TRANSPLANTATION PROCEEDINGS 96 (1990).
Kelemen, et al., 102 INT ARCH ALLERGY IMMUNOL. 309 (1993).
Mengle-Gaw, *The Major Histocompatibility Complex* (MHC), in the ENCYCLOPEDIA OF MOLECULAR BIOLOGY 602-06 (Oxford: Blackwell Science Ltd., 1994).
Rothbard, J. B., et al., 9 ANNU. REV. IMMUNOL. 527 (1991).

Schlegel, et al., 84 BLOOD 2802 (1994).
Sela M et al., 88 BULL INST PASTEUR 303-14 (1990).
Stazl, 22 TRANSPLANTATION PROCEEDINGS 5 (1990).
Sykes, 10 THE FASEB JOURNAL 721 (1996).
Teitelbaum et al., 1 EUR. J. IMMUNOL. 242-48 (1971).
Teitelbaum et al., 3 EUR. J. IMMUNOL. 273-79 (1973).
Teitelbaum et al., 64 J. NEUROIMMUNOL. 209-17 (1996).
Thomson, 10 IMMUNOLOGY TODAY 6 (1988).
Van Den Bogaerde, et al., 52 TRANSPLANTATION 15 (1991).
Webb et al. 13 IMMUNOCHEM. 333 (1976).

SUMMARY OF THE INVENTION

Surprisingly, Copolymer 1 and the Terpolymers of the present invention can be used to treat a variety of autoimmune diseases in a heterogeneous patient population. These Terpolymers can inhibit some of the physiological responses of T cells that attack self-antigens as these diseases progress. Moreover, Copolymer 1 and the Terpolymers of the present invention bind with high affinity to antigen presenting cells from different genetic backgrounds and to several class II MHC molecules to block immune cell recognition and attack. In addition, the Terpolymers can stimulate the growth and functioning of Copolymer 1-specific T cells to further treat and prevent various autoimmune diseases.

Accordingly, the present invention provides a composition having a polypeptide comprising three different amino acids selected from the group of amino acids comprising Copolymer 1, that is, glutamic acid, alanine, lysine, and tyrosine, in the approximate relative molar ratios found in Copolymer 1.

The present invention is also directed to pharmaceutical compositions which include a therapeutically effective amount of a Terpolymer consisting essentially of amino acids tyrosine, alanine and lysine, in the molar ratio of from about 0.005 to about 0.25 tyrosine, from about 0.3 to about 0.6 alanine, and from about 0.1 to about 0.5 lysine, and a pharmaceutically acceptable carrier. This Terpolymer is preferably substantially free of glutamic acid.

The present invention further provides a pharmaceutical composition which includes a therapeutically effective amount of a Terpolymer consisting essentially of glutamic acid, tyrosine and lysine, in the molar ratio of from about 0.005 to about 0.300 glutamic acid, from about 0.005 to about 0.250 tyrosine; and from about 0.3 to about 0.7 lysine, and a pharmaceutically acceptable carrier. The Terpolymer is preferably substantially free of alanine.

The present invention is also directed to pharmaceutical compositions which include a therapeutically effective amount of a Terpolymer consisting essentially of amino acids tyrosine, glutamic acid and alanine in the molar ratio of from about 0.005 to about 0.25 tyrosine, from about 0.005 to about 0.3 glutamic acid, and from about 0.005 to about 0.8 alanine and a pharmaceutically acceptable carrier. This Terpolymer is preferably substantially free of lysine.

The present invention also provides a pharmaceutical composition which includes a therapeutically effective amount of a Terpolymer consisting essentially of glutamic acid, alanine and lysine, in the molar ratio of from about 0.005 to about 0.3 glutamic acid, from about 0.005 to about 0.6 alanine; and from about 0.2 to about 0.7 lysine and a pharmaceutically acceptable carrier. This Terpolymer is preferably substantially free of tyrosine.

The present invention also provides a pharmaceutical composition to treat autoimmune diseases which includes a therapeutically effective amount of Copolymer 1 or a polypeptide consisting essentially of glutamic acid, alanine, tyrosine and lysine, and a pharmaceutically acceptable carrier.

The present invention further provides methods for treating and preventing autoimmune diseases in a mammal which include administering a therapeutically effective amount of a composition comprising Copolymer 1 or a Terpolymer. In another embodiment, the method for treating autoimmune diseases in a mammal further involves inhibiting proliferation of T cells involved in the immune attack. In another embodiment, the method for treating autoimmune diseases in a mammal involves binding the Terpolymer to an antigen presenting cell. In yet another embodiment, the method for treating autoimmune disease in a mammal involves binding the Terpolymer to a major histocompatibility complex class II protein which is associated with autoimmune diseases.

Autoimmune diseases contemplated by the present invention include arthritic conditions, demyelinating diseases and inflammatory diseases. For example, autoimmune diseases which can be treated by the present compositions include multiple sclerosis, autoimmune hemolytic anemia, autoimmune oophoritis, autoimmune thyroiditis, autoimmune uveoretinitis, Crone's disease, chronic immune thrombocytopenic purpura, colitis, contact sensitivity disease, diabetes mellitus, Graves disease, Guillain-Barre's syndrome, Hashimoto's disease, idiopathic myxedema, myasthenia gravis, psoriasis, pemphigus vulgaris, rheumatoid arthritis, or systemic lupus erythematosus. The present compositions can be used to treat one or more of these diseases.

BRIEF DESCRIPTION OF THE DRAWINGS

As used below

"GAL" is a random terpolymer of glutamic acid, alanine and lysine;

"TGA" or "YEA" is a random terpolymer of tyrosine, glutamic acid, and alanine;

"TAL" or "YAK" is a random terpolymer of tyrosine, alanine, and lysine;

"GTL" or "YEK" is a random terpolymer of glutamic acid, tyrosine, and lysine; and "YEAK" is Copolymer 1.

Figure 1A:
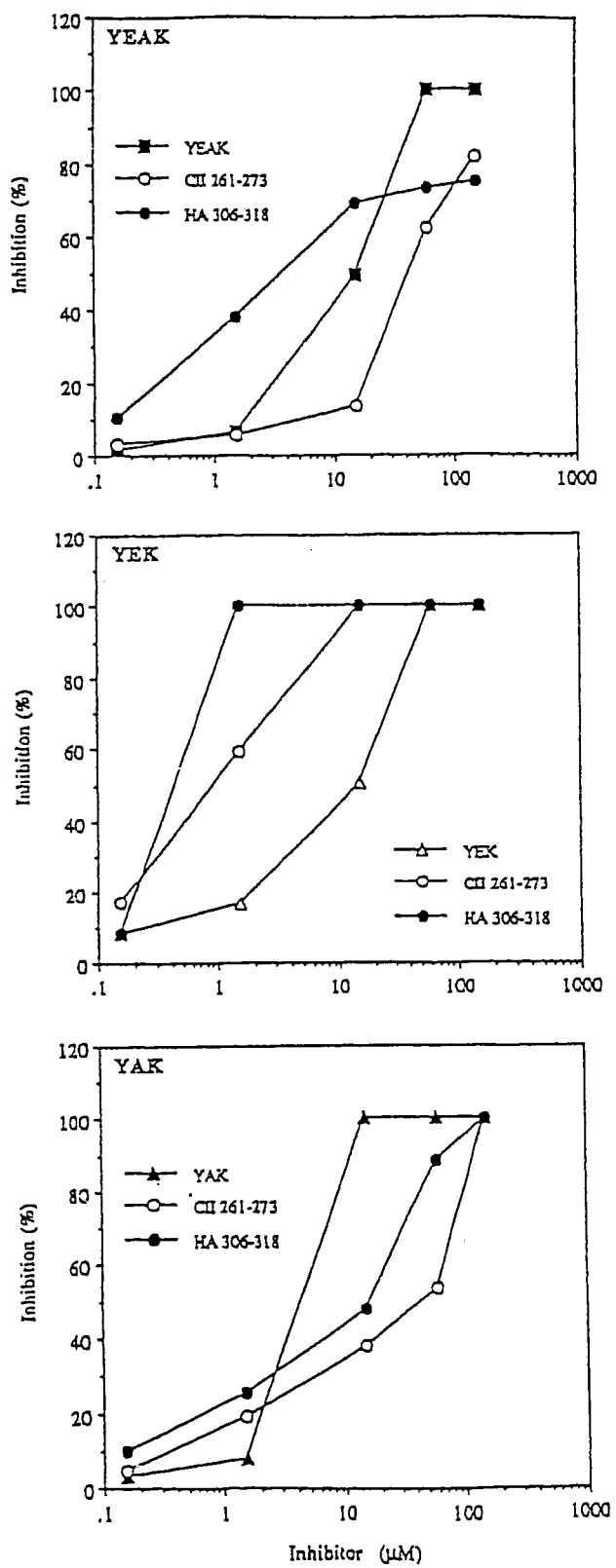
Figure 1B:
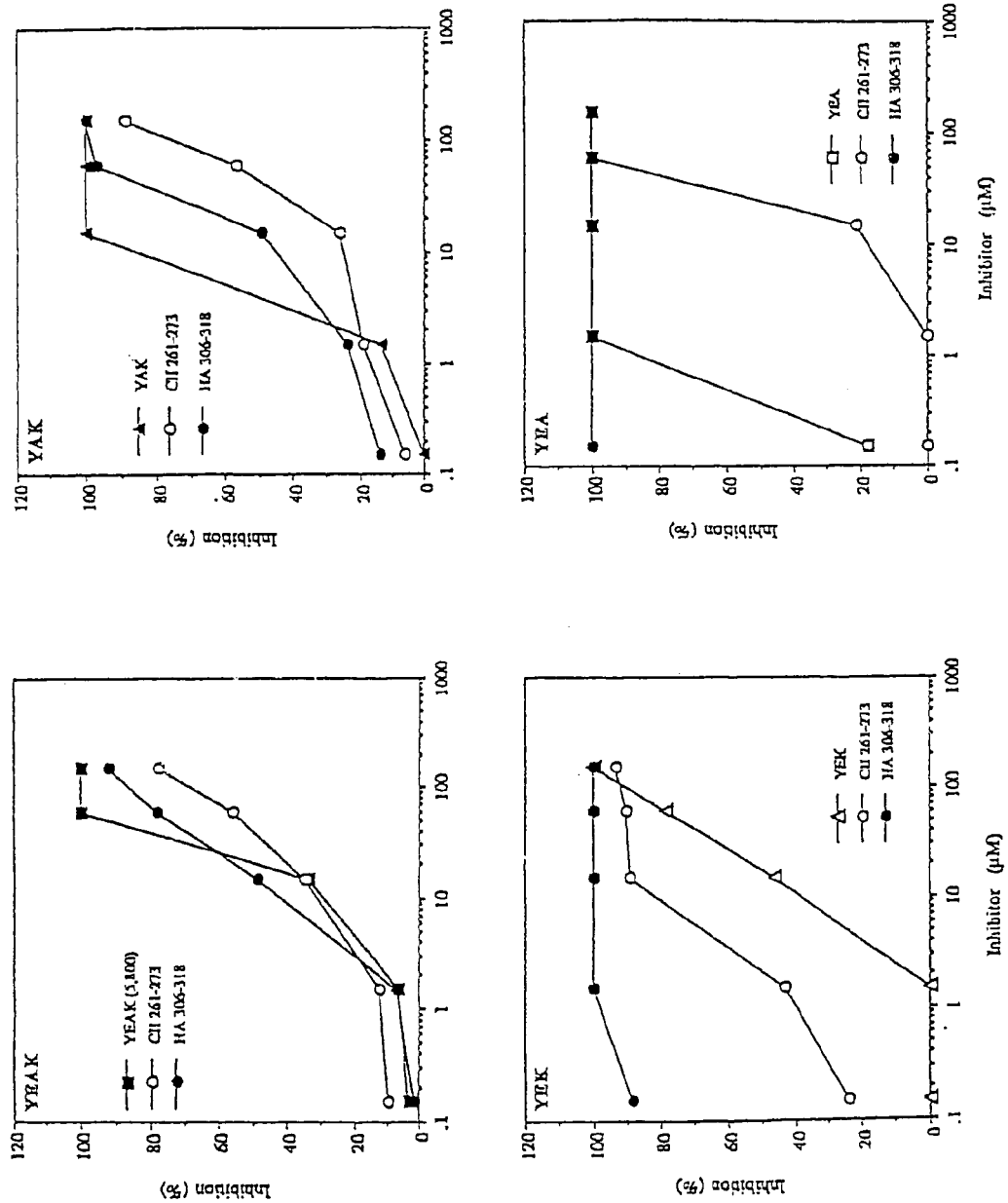

FIG. 1 illustrates the effect of Copolymer 1 and Terpolymers on proliferation of T cells which are specific for certain myelin basic protein (MBP) peptides. Several of the present Terpolymers inhibit proliferation of T cell lines which are specific for myelin basic protein antigen, MBP 84-102 (SEQ ID NO: 1). The following symbols were used: Copolymer 1 (●); GAL (□); TGA (Δ); TAL (o); GTL (X). FIG. 1A illustrates inhibition of the proliferation of mouse T cell clone MBP-sp-1 specific to MBP 84-102 peptide (0.5 g/well). As a control, proliferation of mouse T cell clone MBP-sp-1 stimulated by MBP 84-102 (SEQ ID NO: 1) without inhibitor was 21,145 cpm. FIG. 1B illustrates inhibition of the response of human T cell clone GP-25 to MBP 84-102 peptide (0.125 g/well). Proliferation of human T cell clone GP-25 stimulated by MBP 84-102 (SEQ ID NO: 1) peptide without inhibitor was 11,442 cpm.

Figure 2:
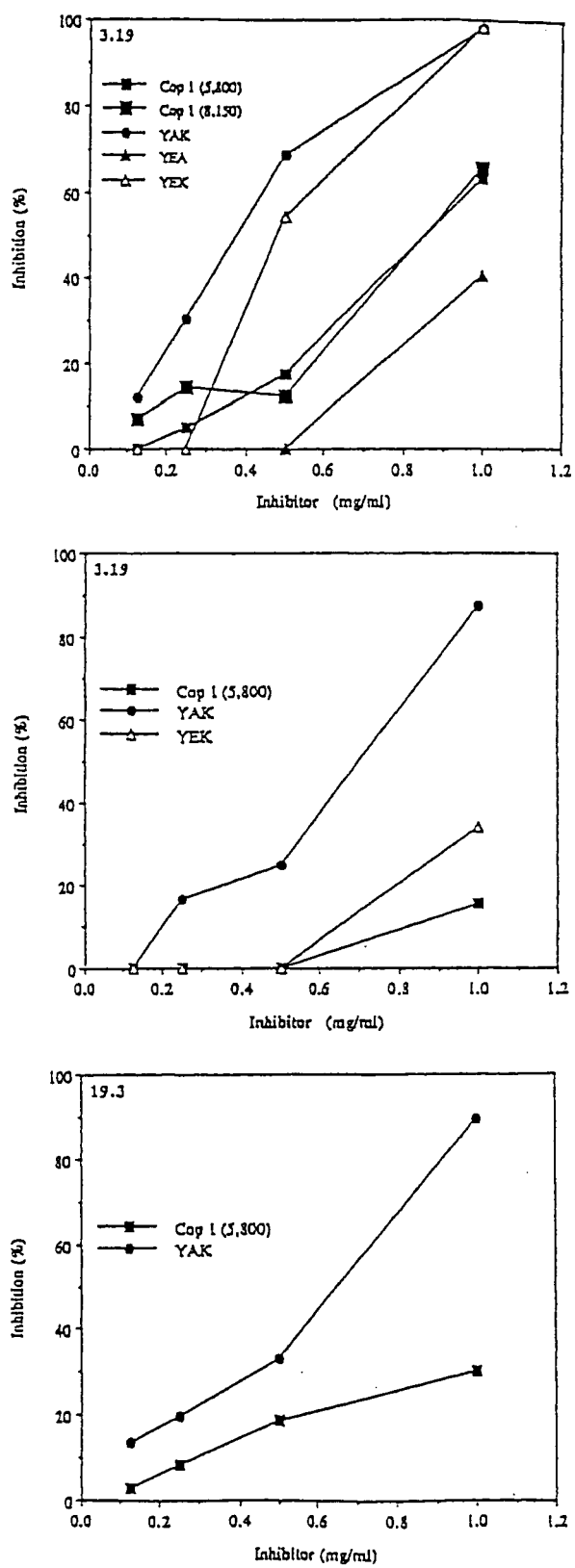

FIG. 2A compares binding of the present polypeptides with the binding of Copolymer 1, to Class II major histocompatibility molecules DR1 (top), DR2 (middle) and DR4 (bottom). Binding by Copolymer 1 (■), was compared to binding by the following biotinylated Terpolymers: GAL (□); TGA (▲); GTL (Δ); and TAL (◆). The amount of Class II major histocompatibility molecule was held constant at 0.5 μg/sample and the concentration of polypeptide was varied between 0-8 µM as indicated on the y-axis. Binding was at pH 5.0 for 40 hr at 37° C. Binding was detected by capturing the polypeptide-class II complexes with an LB3.1 antibody and detecting the amount of biotinylated polypeptide bound by monitoring the absorbency at 410 nm after reaction with streptavidin-conjugated alkaline phosphatase.

FIG. 2B provides Lineweaver-Burke plots of the binding data provided in FIG. 2A.

Figure 3A:
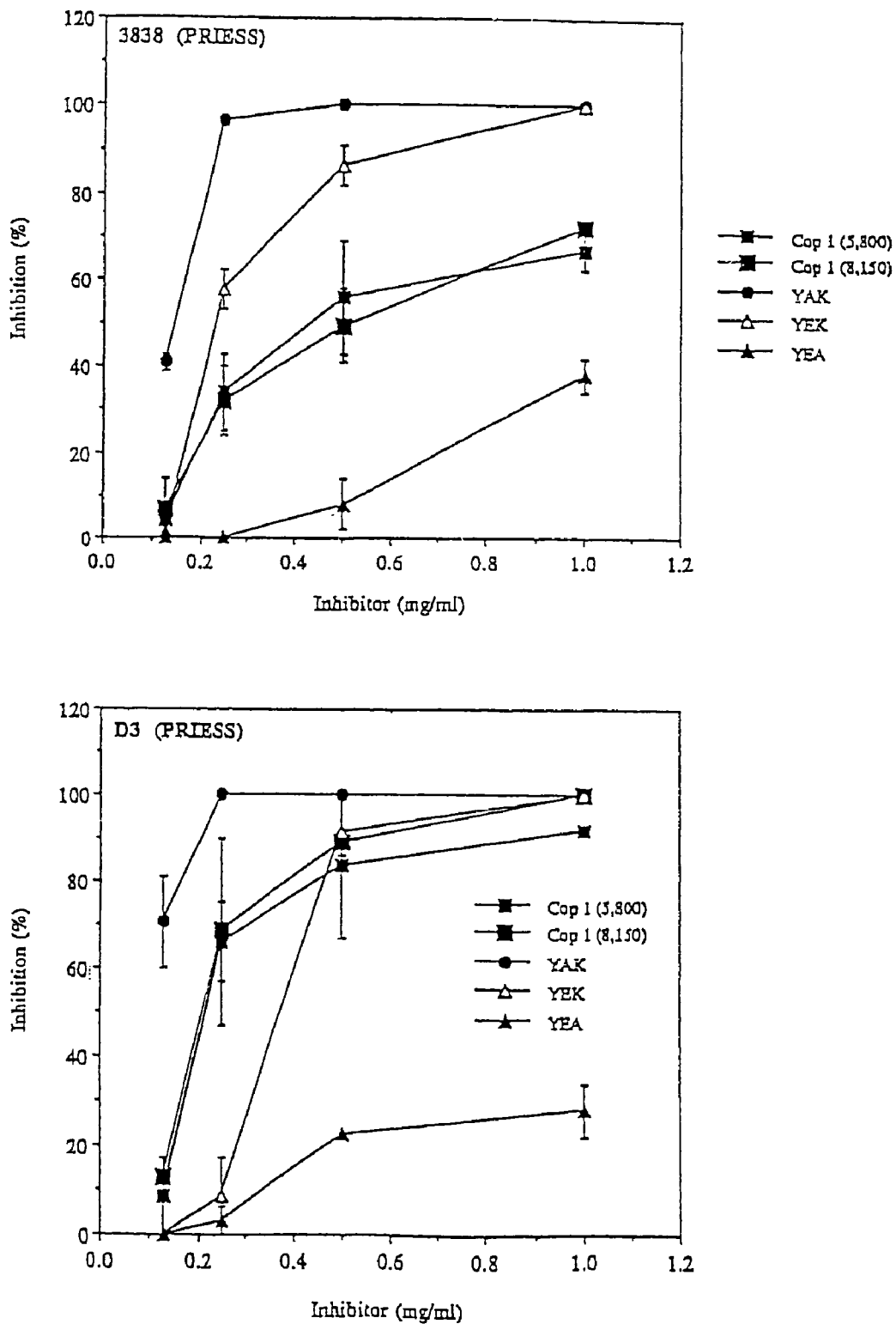
Figure 3B:
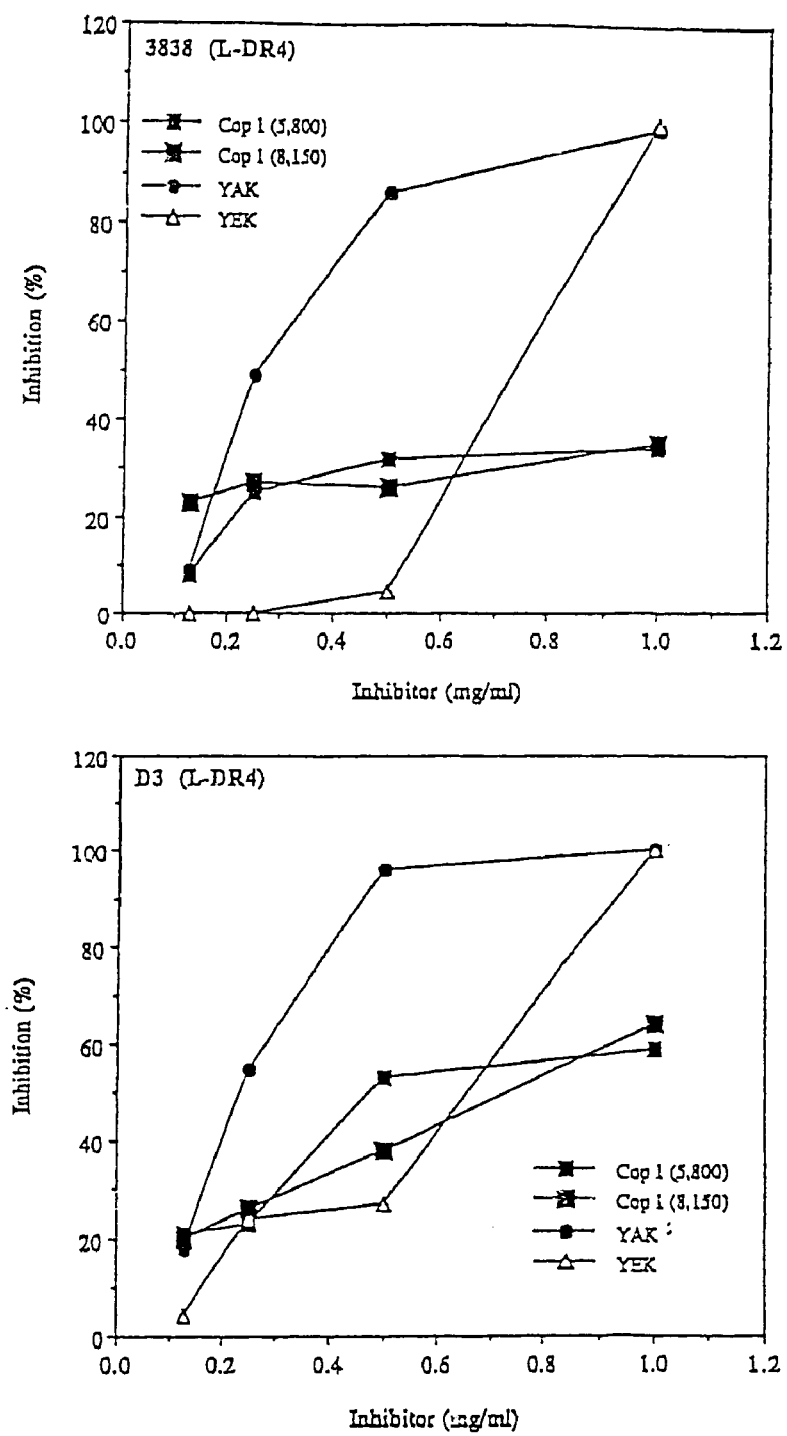

FIG. 3 illustrates the competitive inhibition of Copolymer 1 binding to Class II major histocompatibility molecules by the present polypeptides. Purified HLA-DR1 (top), HLA-DR2 (middle) and HLA-DR4 (bottom) molecules were incubated with a constant amount (1.5 µM) of biotinylated Copolymer 1, either alone or in the presence of one of the following unlabeled polypeptides: Copolymer 1 (■); GAL (□); TGA (▲); GTL (Δ); and TAL (♦). Inhibition by these polypeptides was compared to inhibition by the myelin basic protein antigen HA 306-318 (0) (SEQ ID NO: 2). Binding was at pH 5.0 for 40 hr at 37° C. The amount of unlabeled polypeptide was varied between 0.1-1000 µM, as indicated on the y-axis. Specific binding is expressed as the percentage of inhibition using equation 1:

$$\text{percent inhibition} = 100 - \frac{(\text{signal with competitor} - \text{background})}{(\text{signal without competitor} - \text{background})} \times 100 \qquad 1$$

Figure 4A:
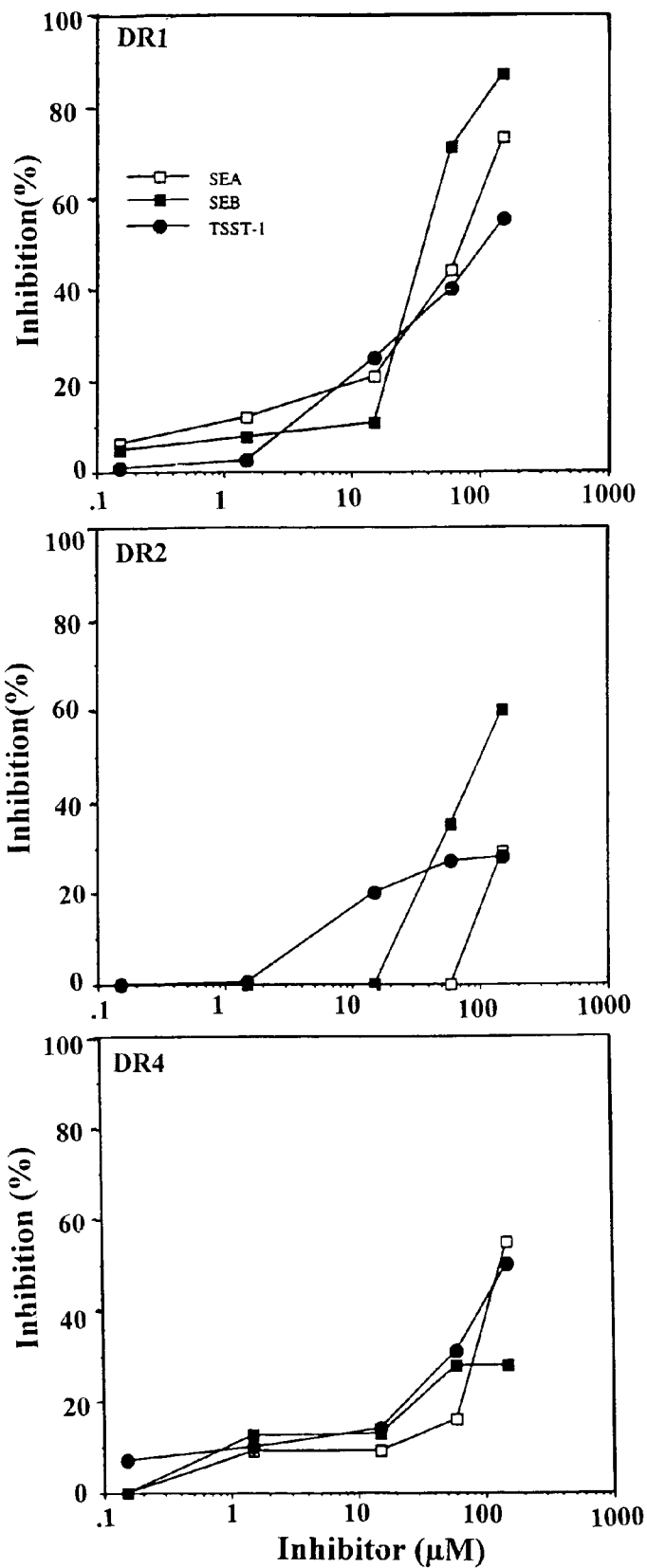

FIG. 4A illustrates the competitive inhibition of TAL binding to Class II major histocompatibility molecules by bacterial superantigens SEA, SEB and TSST-1. Purified HLA-DR1 (top), HLA-DR2 (middle) and HLA-DR4 (bottom) molecules were incubated with a constant amount of biotinylated TAL, in the presence of increasing amounts of unlabeled bacterial superantigen SEA (□); SEB (■); or TSST-1 (●). Binding was at pH 5.0 for 40 hr at 37° C. The amount of superantigen was varied between 0.1-1000 µM, as indicated on the y-axis. Specific binding is expressed as the percentage of inhibition using equation 1.

Figure 4B:
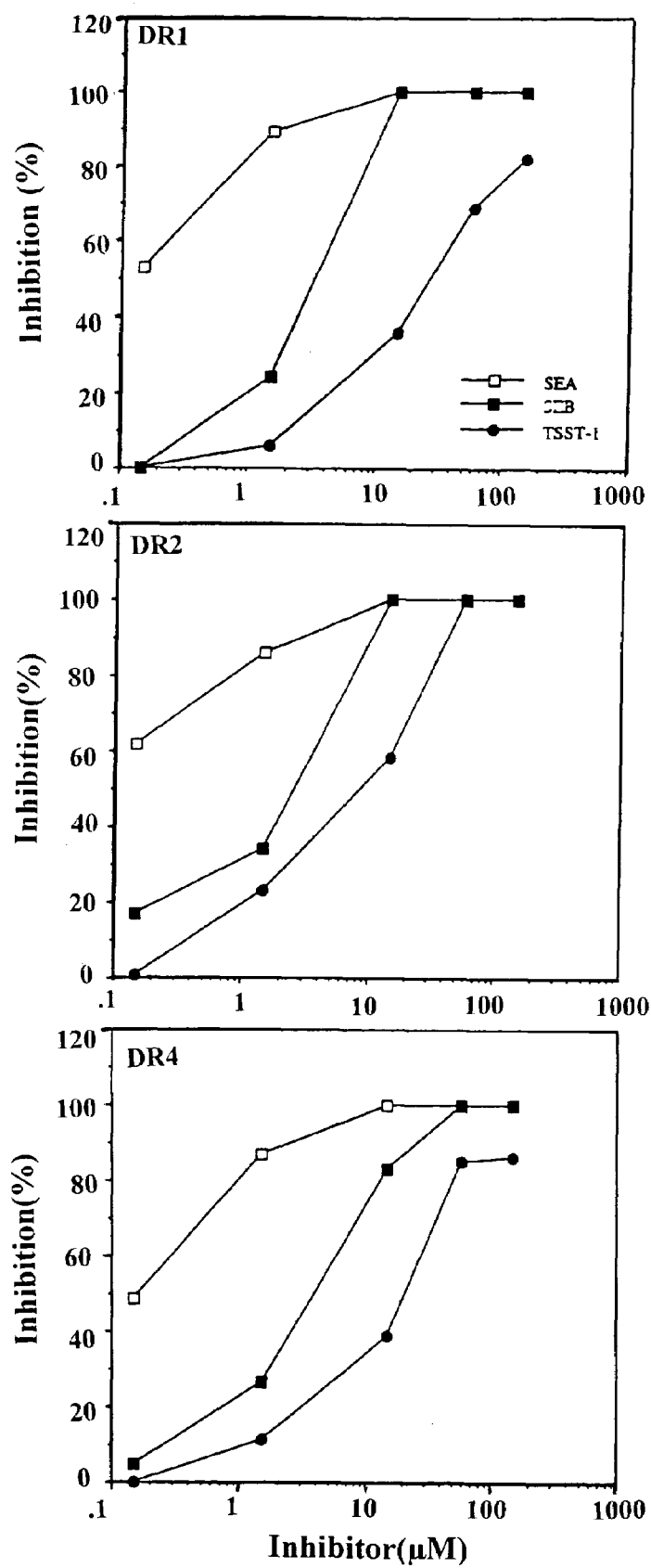

FIG. 4B illustrates the competitive inhibition of TGA binding to Class II major histocompatibility molecules by bacterial superantigens SEA, SEB and TSST-1. Purified HLA-DR1 (top), HLA-DR2 (middle) and HLA-DR4 (bottom) molecules were incubated with a constant amount of biotinylated polypeptide TGA, in the presence of increasing amounts of unlabeled bacterial superantigen SEA (□); SEB (■); or TSST-1 (●). Binding was at pH 5.0 for 40 hr at 37° C. The amount of superantigen was varied between 0.1-1000 µM, as indicated on the y-axis. Specific binding is expressed as the percentage of inhibition, calculated according to equation above 1.

Figure 4C:
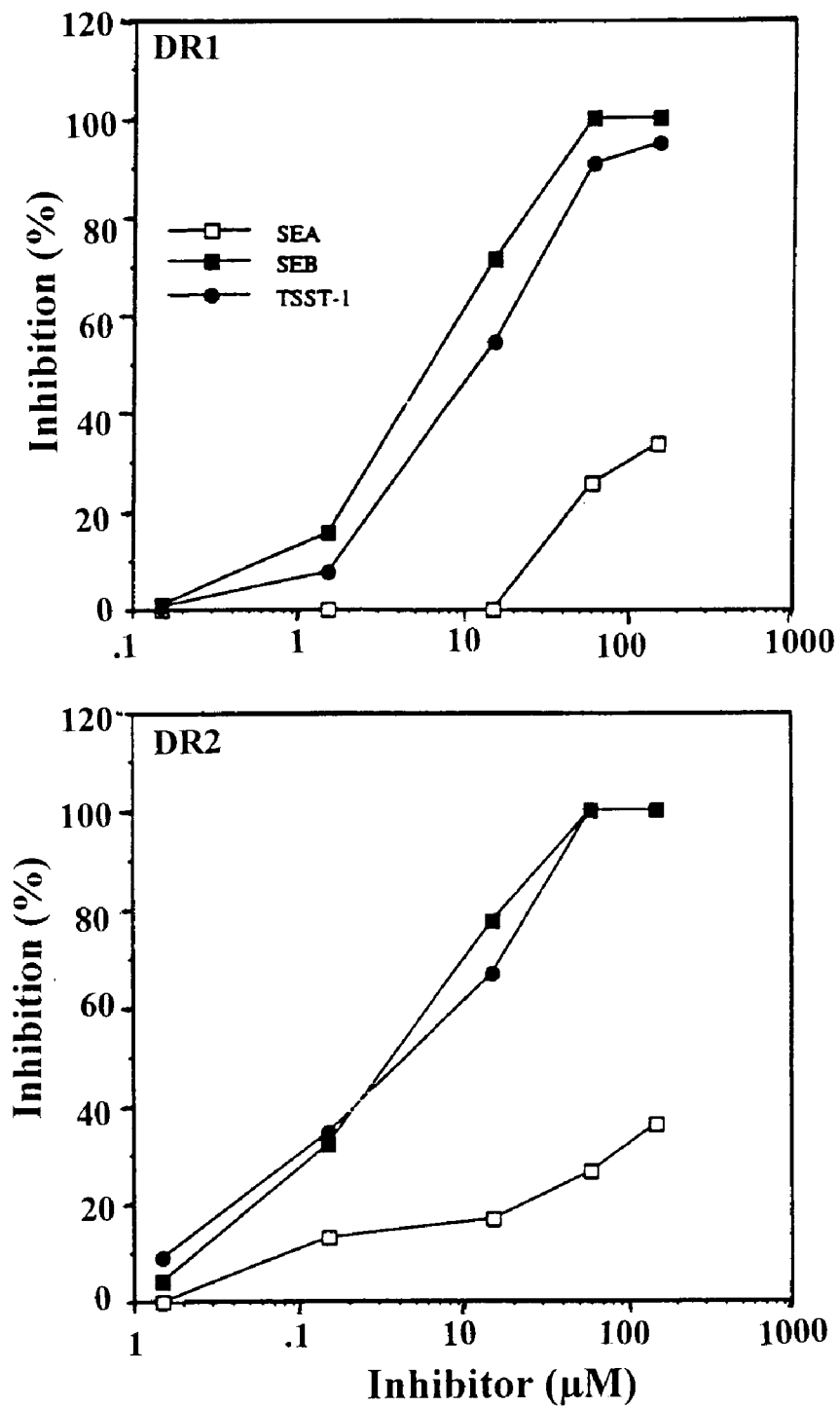

FIG. 4C illustrates the competitive inhibition of GAL binding to Class II major histocompatibility molecules by bacterial superantigens SEA, SEB and TSST-1. Purified HLA-DR1 (top), and HLA-DR2 (bottom) molecules were incubated with a constant amount of biotinylated GAL, in the presence of increasing amounts of unlabeled bacterial superantigen SEA (□); SEB (■); or TSST-1 (●). Binding was at pH 5.0 for 40 hr at 37° C. The amount of superantigen was varied between 0.1-1000 µM, as indicated on the y-axis. Specific binding is expressed as the percentage of inhibition using equation 1 above.

Figure 5A:
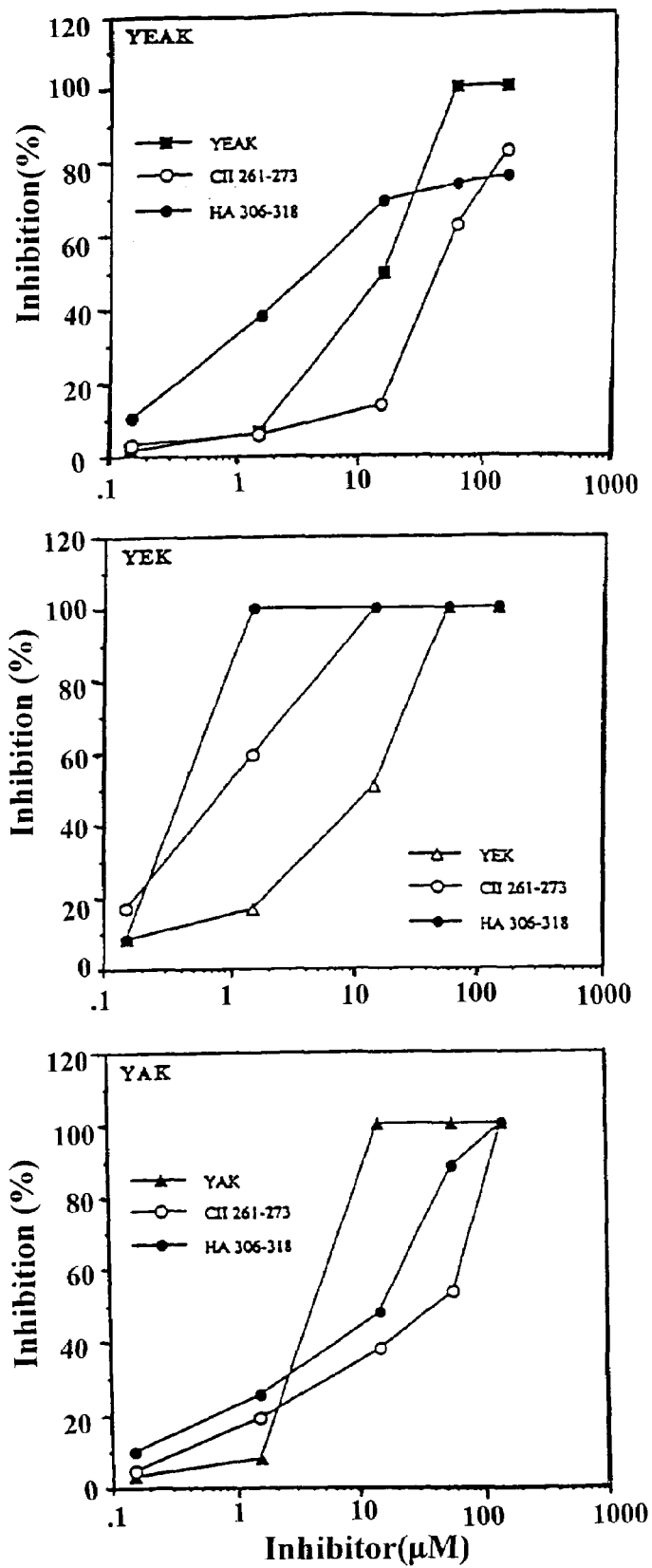
Figure 5B:
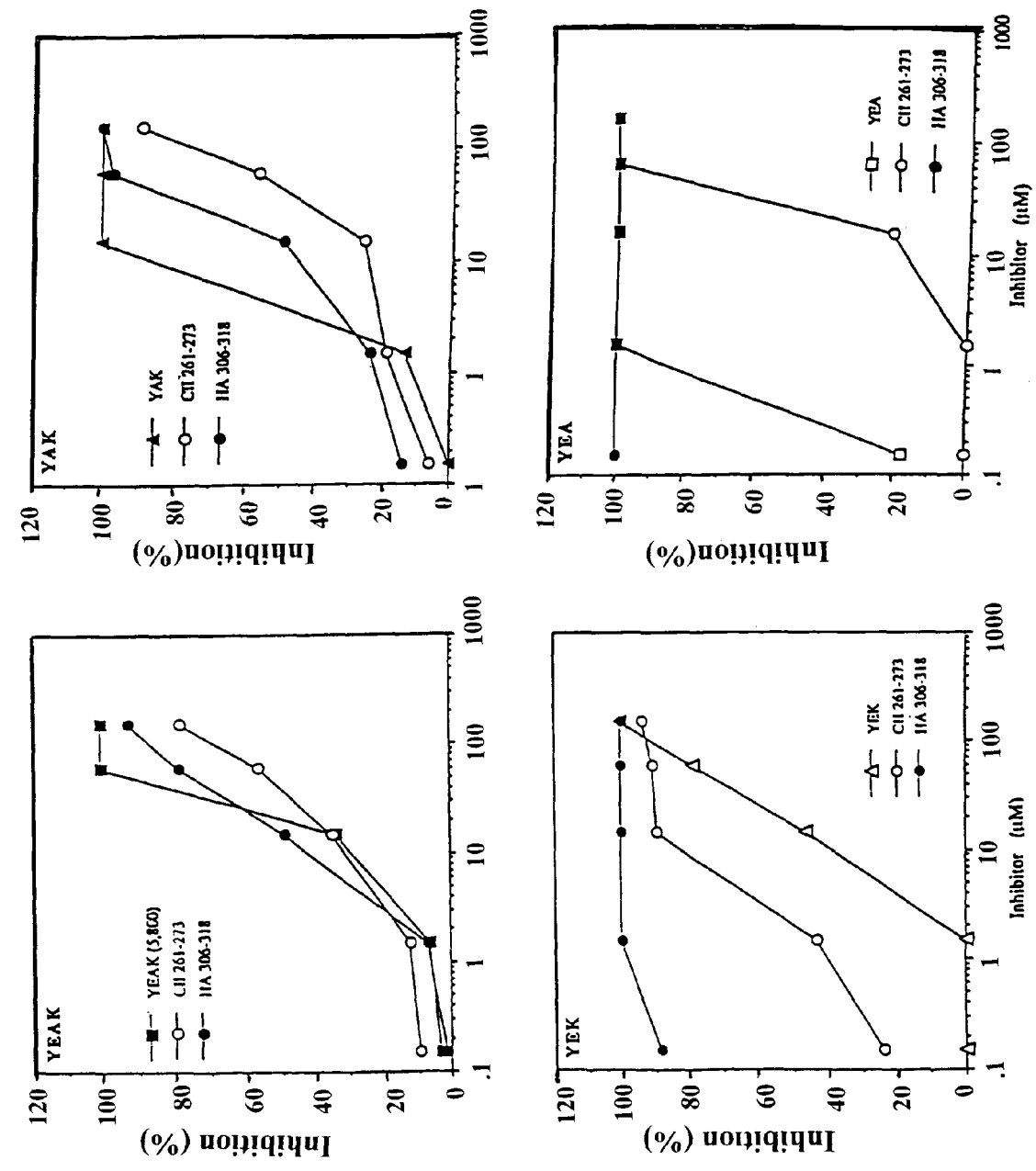

FIG. 5 shows inhibition of binding of labeled molecules to MHC class II purified proteins by Terpolymers of the present invention. FIG. 5A shows inhibition of binding to the MHC HLA-DR1 protein. FIG. 5B shows inhibition of binding to the MHC HLA-DR4 protein. Unlabeled competitors include Terpolymers of the present invention, influenza virus hemagglutinin (HA) peptide 306-318 (SEQ ID NO:2), and type II collagen (CII) peptide 261-273 (SEQ ID NO:3). The concentration of unlabeled competitor is indicated on the abscissa. In each panel, inhibition by CII 261-273 (SEQ ID NO:3) is shown as open circles (○), inhibition by HA 306-318 (SEQ ID NO: 2) is shown by solid circles (●), inhibition by one of the present terpolymers is indicated as shown by open or solid triangles or squares. The extent of inhibition by GTL is shown using open triangles (Δ), by TAL is shown as solid triangles (▲), by TGA as open squares (□), and by Copolymer 1 as solid squares (■). Specific binding observed and shown on the ordinate was calculated as percentage of inhibition using equation 1 above.

Figure 6:
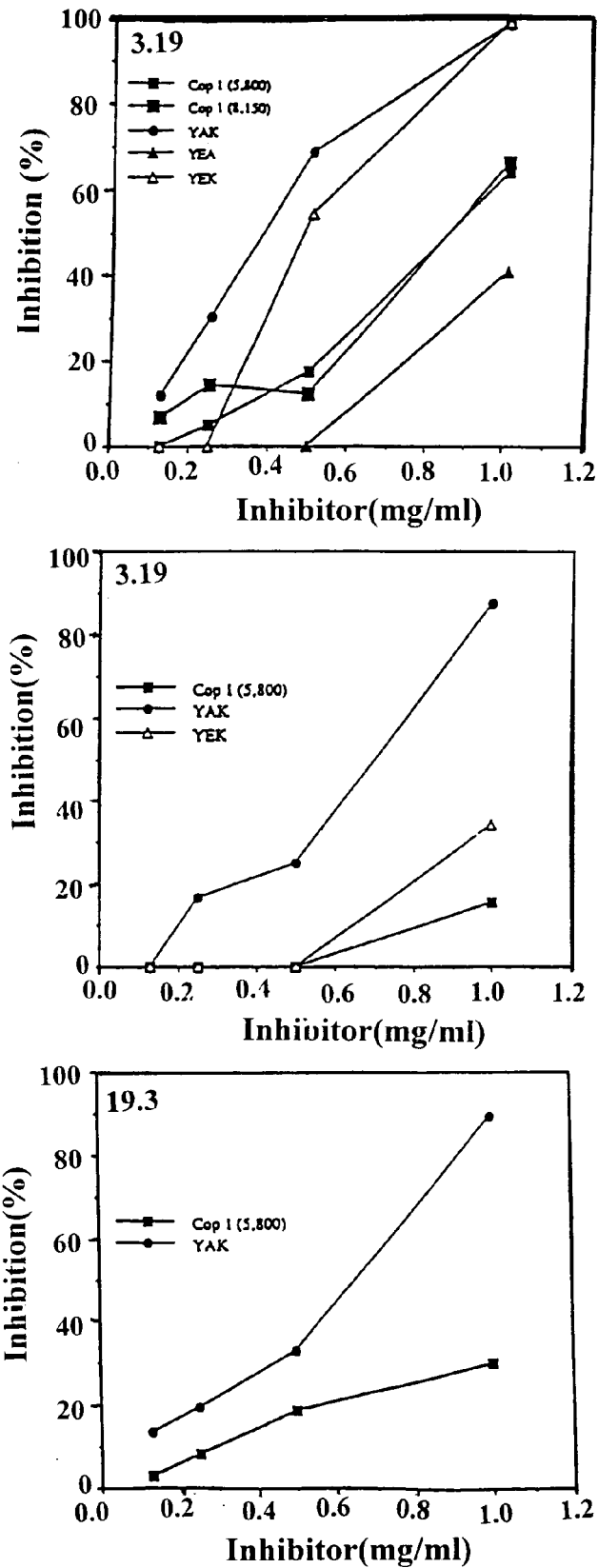

FIG. 6 shows inhibition of IL-2 production by DR1-restricted-CII-specific T cell hybridomas in the presence of different polypeptides of the present invention. Irradiated L57.23 cells (fibroblasts transfected with a gene encoding HLA-DR1) were coincubated in duplicate with collagen peptide CII 261-273 (40 µg/ml) and varying concentrations, shown on the abscissa, of one of the present polypeptides for 2 hr at 37° C., then T cells (clone 3.19 or 19.3 as indicated) were added, and the mixtures were further incubated for 24 hr at 37° C. Supernatants (30 µl) were then removed, and were assayed for activation by IL-2-induced proliferation of IL-2-dependent cytotoxic T lymphocytes (CTL-L). The extent of inhibition by TAL is shown as solid circles (●), by TGA as solid triangles (▲), by GTL as open triangles (Δ), and by Copolymer 1 as solid squares (■). Percent inhibition of CTL-L proliferation shown on the ordinate was calculated according to equation 1.

Figure 7A:
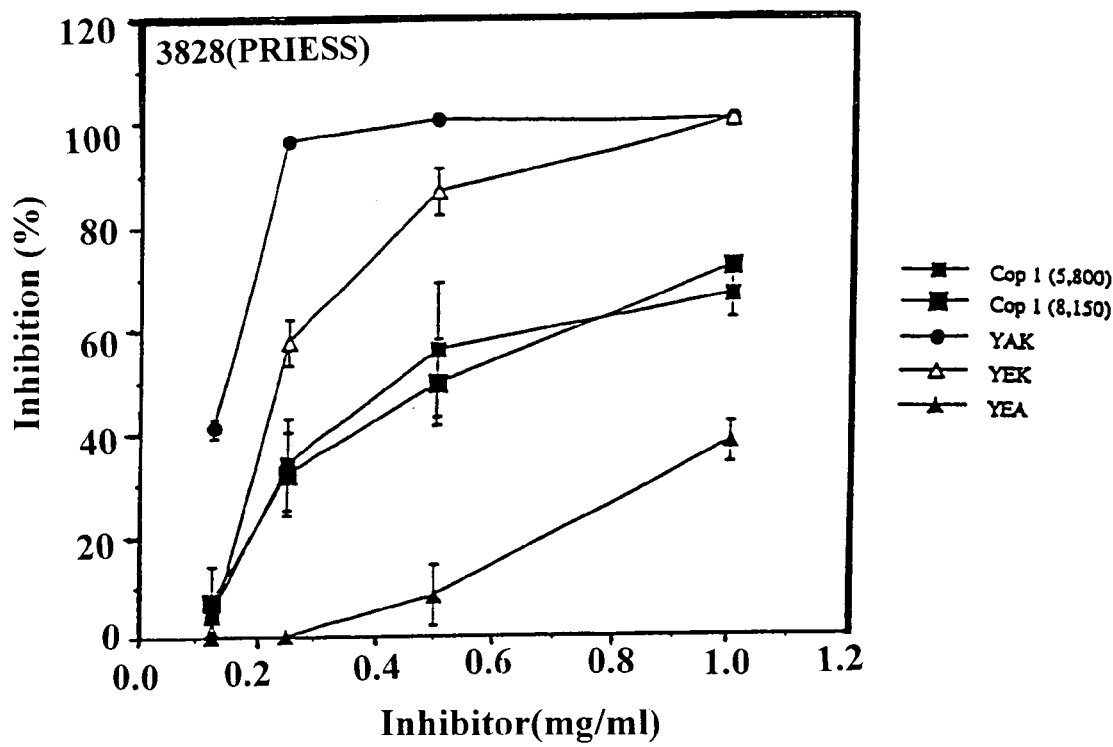
Figure 7A:
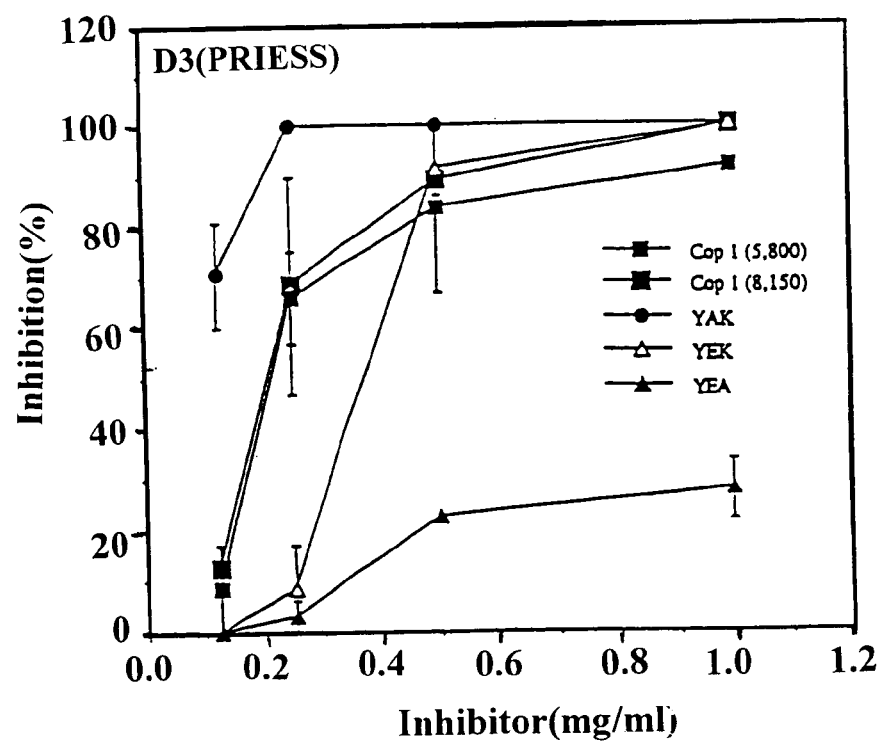
Figure 7B:
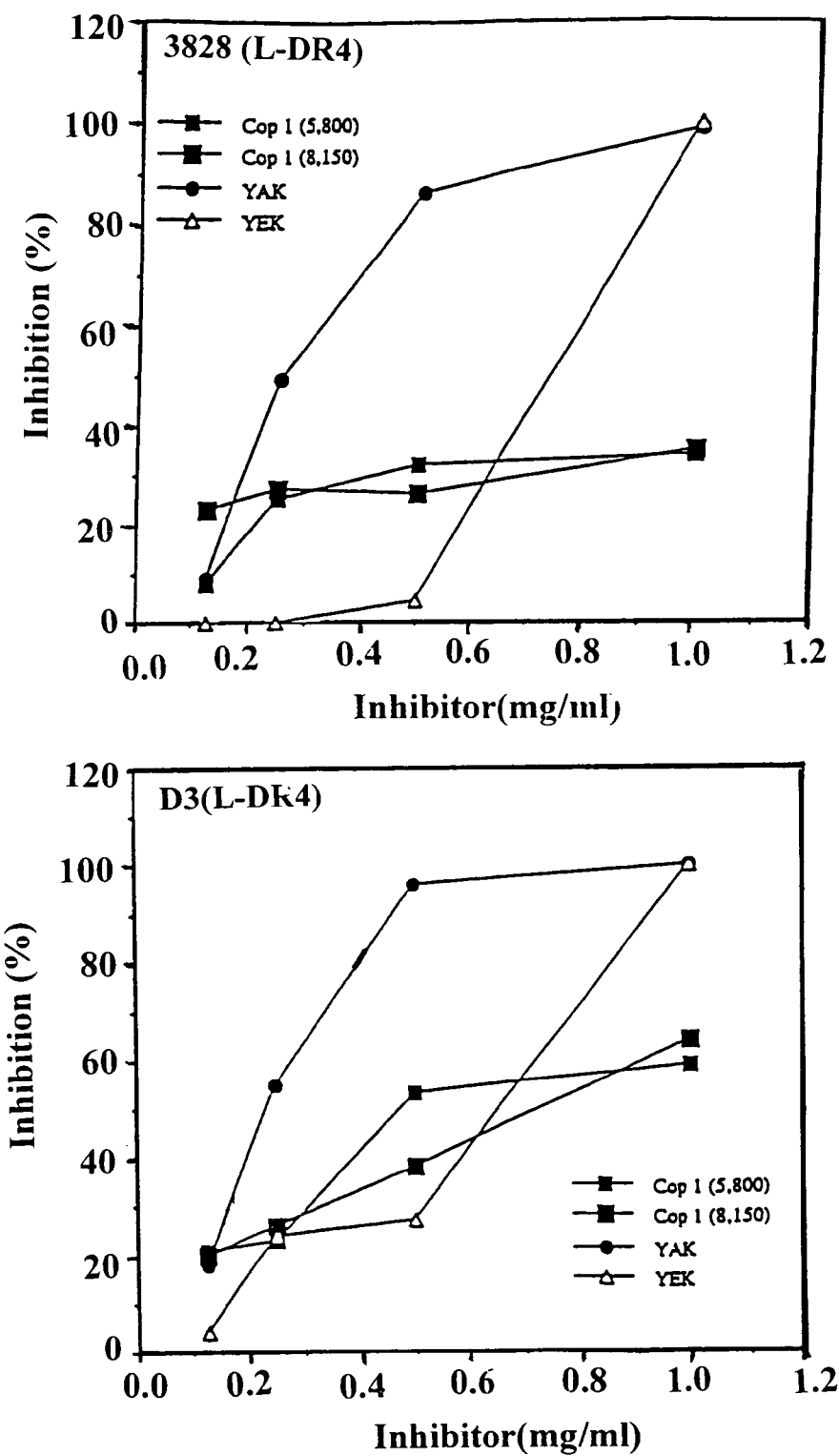

FIG. 7 shows inhibition of IL-2 production by DR4-restricted CII-specific T cell hybridomas (3838 and D3) in the presence of different polypeptides of the present invention. FIG. 7A shows the effects of coincubating irradiated 3838 or D3 Priess cells with collagen peptide CII 261-273 (SEQ ID NO: 3) at the fixed concentration of 40 µg/ml, and with varying concentrations of each of the present polypeptides, for 2 hr at 37° C. FIG. 7B shows the effects of incubating L cells transfected with a gene encoding HIA-DR4 with collagen peptide CII 261-273 (SEQ ID NO:3) at the fixed concentration of 40 µg/ml, and with varying concentrations of each of the present polypeptides, for 2 hr at 37° C. T cells were then added (clones 3838 or D3 as indicated), samples were further incubated for 24 hr at 37° C., and supernatants were assayed as described in FIG. 6. Each polypeptide was tested in duplicate. The concentration of the present polypeptides is indicated on the abscissa. The same symbols as used in FIG. 6 are used for this figure.

DETAILED DESCRIPTION OF THE INVENTION

According to the present invention, polypeptides having at least three different amino acids randomly polymerized in a linear configuration are useful for treating autoimmune diseases. Autoimmune diseases occur when the immune system inappropriately attacks certain tissues or cells. The polypeptides of the present invention can prevent the immune system from attacking, for example, by suppressing the proliferation or function of T or B cells responsible for the attack, or by shielding the tissue from attack by binding to a MHC protein on the surface of the cells that make up the tissue.

Amino acids of the present invention include, but are not limited to the 20 commonly occurring amino acids. Also included are naturally occurring and synthetic derivatives, for example, selenocysteine. Amino acids further include amino acid analogs. An amino acid "analog" is a chemically related form of the amino acid having a different configuration, for example, an isomer, or a D-configuration rather than an L-configuration, or an organic molecule with the approximate size and shape of the amino acid, or an amino acid with modification to the atoms that are involved in the peptide bond, so as to be protease resistant when polymerized in a polypeptide.

The phrases "amino acid" and "amino acid sequence" as defined here and in the claims can include one or more components which are amino acid derivatives and/or amino acid analogs comprising part or the entirety of the residues for any one or more of the 20 naturally occurring amino acids indicated by that sequence. For example, in an amino acid sequence having one or more tyrosine residues, a portion of one or more of those residues can be substituted with homotyrosine. Further, an amino acid sequence having one or more non-peptide or peptidomimetic bonds between two adjacent residues, is included within this definition.

The one letter and three letter amino acid codes (and the amino acid that each represents) are as follows: A means ala (alanine); C means cys (cysteine); D means asp (aspartic acid); E means glu (glutamic acid); F means phe (phenylalanine); G means gly (glycine); H means his (histidine); I means ile (isoleucine); K means lys (lysine); L means leu (leucine); M means met (methionine); N means asn (asparagine); P means pro (proline); Q means gin (glutamine); R means arg (arginine); S means ser (serine); T means thr (threonine); V means val (valine); W means trp (tryptophan); and Y means tyr (tyrosine).

The term "hydrophobic" amino acid is defined here and in the claims as including aliphatic amino acids alanine (A, or ala), glycine (G, or gly), isoleucine (I, or ile), leucine (L, or leu), proline (P, or pro), and valine (V, or val), the terms in parentheses being the one letter and three letter standard code abbreviations for each amino acid, and aromatic amino acids tryptophan (W, or trp), phenylalanine (F or phe), and tyrosine (Y, or tyr). The amino acids confer hydrophobicity as a function of the length of aliphatic and size of aromatic side chains, when found as residues within a protein.

The term "charged" amino acid is defined here and in the claims as including amino acids aspartic acid (D, or asp), glutamic acid (E, or glu), histidine (H, or his), arginine (R, or arg) and lysine (K, or lys), which confer a positive (his, lys and arg) or negative (asp and gly) charge at physiological values of pH in aqueous solutions on proteins containing these residues.

Polypeptide Compositions Contemplated by the Invention

The polypeptides of the present invention comprise Copolymer 1 and Terpolymers consisting essentially of three of the four amino acids of Copolymer 1, namely tyrosine, glutamic acid, alanine and lysine. However, one of skill in the art can readily substitute structurally-related and/or charge-related amino acids without deviating from the spirit of the invention. Thus, the present invention further contemplates conservative amino acid substitutions for tyrosine, glutamic acid, alanine and lysine in the present polypeptides. Such conservative substitutions are structurally-related amino acid substitutions, including those amino acids which have about the same charge, hydrophobicity and size as tyrosine, glutamic acid, alanine or lysine. For example, lysine is structurally-related to arginine and histidine; glutamic acid is structurally-related to aspartic acid; tyrosine is structurally-related to serine, threonine, phenylalanine and tryptophan; and alanine is structurally-related to valine, leucine and isoleucine. These and other conservative substitutions, such as structurally-related synthetic amino acids, are contemplated by the present invention.

Moreover, the Terpolymers can be composed of I- or d-amino acids. As is known by one of skill in the art, I-amino acids occur in most natural proteins. However, d-amino acids are commercially available and can be substituted for some or all of the amino acids used to make the Terpolymers. The present invention contemplates Terpolymers formed from mixtures of d- and I-amino acids, as well as Terpolymers consisting essentially of either I- or d-amino acids.

The average molecular weight and the average molar fraction of the amino acids in the Terpolymers can vary. However, an average molecular weight range of about 2,000 to about 40,000 daltons is contemplated. A preferred average molecular weight range is from about 4,000 to about 12,000 daltons. Preferred average molecular weight ranges and processes of making the Terpolymers are described in U.S. Pat. No. 5,800,808, which is hereby incorporated by reference in its entirety.

In one embodiment, the present invention provides Terpolymers containing tyrosine, alanine and lysine. The average molar fraction of the amino acids in these Terpolymers can vary, for example, tyrosine can be present in a mole fraction of about 0.005 to about 0.250; alanine can be present in a mole fraction of about 0.3 to about 0.6; and lysine can be present in a mole fraction of about 0.1 to about 0.5. The average molecular weight is between 2,000 to about 40,000 daltons and preferably between about 3,000 to about 35,000 daltons. In a more preferred embodiment, the average molecular weight is about 5,000 to about 25,000 daltons.

In another embodiment, the present invention provides Terpolymers containing tyrosine, glutamic acid and lysine. The average molar fraction of the amino acids in these polypeptides can also vary, for example, glutamic acid can be present in a mole fraction of about 0.005 to about 0.300, tyrosine can be present in a mole fraction of about 0.005 to about 0.250; lysine can be present in a mole fraction of about 0.3 to about 0.7. The average molecular weight is between 2,000 to about 40,000 daltons and preferably between about 3,000 to about 35,000 daltons. In a more preferred embodiment, the average molecular weight is about 5,000 to about 25,000 daltons.

In another embodiment, the present invention provides Terpolymers containing glutamic acid, alanine and lysine. The average molar fraction of the amino acids in these polypeptides can also vary, for example, glutamic acid can be present in a mole fraction of about 0.005 to about 0.300, alanine can be present in a mole fraction of about 0.005 to about 0.600; lysine can be present in a mole fraction of about 0.2 to about 0.7. The average molecular weight is between 2,000 to about 40,000 daltons and preferably between about 3,000 to about 35,000 daltons. In a more preferred embodiment, the average molecular weight is about 5,000 to about 25,000 daltons.

In another embodiment, the present invention provides Terpolymers containing tyrosine, glutamic acid and alanine. The average molar fraction of the amino acids in these polypeptides can also vary, for example, tyrosine can be present in a mole fraction of about 0.005 to about 0.250; glutamic acid can be present in a mole fraction of about 0.005 to about 0.300; and alanine can be present in a mole fraction of about 0.005 to about 0.800. The average molecular weight is between 2,000 to about 40,000 daltons and preferably between about 3,000 to about 35,000 daltons. In a more preferred embodiment, the average molecular weight is about 5,000 to about 25,000 daltons.

In a more preferred embodiment, the mole fraction of amino acids of the Terpolymers is about what is preferred for Copolymer 1. The mole fraction of amino acids in Copolymer 1 is glutamic acid (about 0.14), alanine (about 0.43), tyrosine (about 0.10) and lysine (about 0.34). The most preferred average molecular weight for Copolymer 1 is between about 5,000 and about 9,000 daltons.

The molar ratios of the monomers of the more preferred terpolymer of glutamic acid, alanine and tyrosine is about 0.21 to about 0.65 to about 0.14.

The molar ratios of the monomers of the more preferred terpolymer of glutamic acid, alanine and lysine is about 0.15 to about 0.48 to about 0.36.

The molar ratios of the monomers of the more preferred terpolymer of glutamic acid, tyrosine, and lysine is about 0.26 to about 0.16 to about 0.58.

The molar ratios of the monomers of the more preferred terpolymer of tyrosine, alanine and lysine is about 0.10 to about 0.54 to about 0.35.

In one embodiment, the Terpolymers of the present invention are capable of binding to an MHC class II protein which, preferably, is associated with an autoimmune disease. Any available method can be used to ascertain whether the Terpolymer binds to one or more MHC class II proteins. For example, the polypeptide can be labeled with a reporter molecule (such as a radionuclide or biotin), mixed with a crude or pure preparation of MHC class II protein and binding is detected if the reporter molecule adheres to the MHC class II protein after removal of the unbound polypeptide.

In another embodiment, the Terpolymers of the invention are capable of binding to an MHC class II protein associated with multiple sclerosis. A polypeptide of this embodiment can have similar or greater affinity for the antigen binding groove of an MHC class II protein associated with multiple sclerosis than does Copolymer 1. Hence, the contemplated polypeptide can inhibit binding of or displace the binding of myelin autoantigens from the MHC class II protein. One MHC class II protein associated with multiple sclerosis is HLA-DR4 (DRB1*1501).

In another embodiment, Copolymer 1 and the Terpolymers of the invention are capable of binding to an MHC class II protein associated with an arthritic condition, for example, rheumatoid arthritis or osteoarthritis. Copolymer 1 or a Terpolymer of this embodiment can have a greater affinity for the antigen binding groove of an MHC class II protein associated with the autoimmune disease than does a type II collagen 261-273 (SEQ ID NO:3) peptide. Hence, the contemplated Copolymer 1 or Terpolymers can inhibit binding of or displace the type II collagen 261-273 peptide from the antigen binding groove of an MHC class II protein. The Class II MHC protein consists of approximately equal-sized α and β subunits, both of which are transmembrane proteins. A peptide-binding cleft is formed by parts of the amino termini of both α and β subunits. This peptide-binding cleft is the site of presentation of the antigen to T cells. There are at least three types of Class II MHC molecules: HLA-DR, HLA-DQ, and HLA-DP molecules. There are also numerous alleles encoding each type of these HLA molecules. The Class II MHC molecules are expressed predominantly on the surfaces of B lymphocytes and antigen presenting cells such as macrophages.

The present Terpolymers can be formulated into pharmaceutical compositions containing a pharmaceutically acceptable carrier. As used herein, "pharmaceutically acceptable carrier" includes any and all solvents, dispersion media, coatings, antibacterial and antifungal agents, isotonic and absorption delaying agents, sweeteners and the like. The pharmaceutically acceptable carriers may be prepared from a wide range of materials including, but not limited to, flavoring agents, sweetening agents and miscellaneous materials such as buffers and absorbents that may be needed in order to prepare a particular therapeutic composition. The use of such media and agents with pharmaceutically active substances is well known in the art. Except insofar as any conventional media or agent is incompatible with the active ingredient, its use in the therapeutic compositions is contemplated. Supplementary active ingredients can also be incorporated into the compositions. The present compositions may be formulated as an injectable solution or suspension, a spray solution or a suspension.

Therapeutic Methods Contemplated by the Invention

The present invention further provides methods for treating and preventing autoimmune diseases in a mammal which include administering a therapeutically effective amount of a composition having a polypeptide containing at least three different amino acids selected from the group consisting of the amino acids which comprise Copolymer 1, namely glutamic acid, tyrosine, lysine, and alanine, wherein the selected amino acids are randomly polymerized in a linear configuration. In one embodiment the polypeptide is Copolymer 1 or a Terpolymer.

Autoimmune diseases contemplated by the present invention include either cell-mediated disease (e.g. T-cell) or antibody-mediated (e.g. B cell) disorders. Such disorders can be inter alia arthritic conditions, demyelinating diseases and inflammatory diseases. For example, autoimmune diseases which can be treated by the present polypeptides include multiple sclerosis, autoimmune hemolytic anemia, autoimmune oophoritis, autoimmune thyroiditis, autoimmune uveoretinitis, Crohn's disease, chronic immune thrombocytopenic purpura, colitis, contact sensitivity disease, diabetes mellitus, Graves disease, Guillain-Barre's syndrome, Hashimoto's disease, idiopathic myxedema, myasthenia gravis, psoriasis, pemphigus vulgaris, rheumatoid arthritis, or systemic lupus erythematosus, The present compositions can be used to treat one or more of these diseases.

The term "arthritic condition" as used herein is a condition wherein at least one symptom of rheumatoid arthritis is observed in at least one joint of a mammal, for example in a shoulder, knee, hip, backbone or a digit of the mammal. Examples of arthritic conditions include "Polyarthritis", which is an arthritic condition that affects more than a single joint; "juvenile arthritis", an arthritic condition of humans under the age of 21; and Felty's syndrome, which can include the symptoms of neutropenia, splenomegaly, weight loss, anemia, lymphadenopathy, and pigment spots on the skin.

In one embodiment, any autoimmune disease can be treated by the present polypeptides so long as the contemplated polypeptide binds to an MHC class II protein that has been associated with the autoimmune disease. One aspect of this embodiment provides a method which includes selecting a polypeptide that inhibits binding of an antigenic peptide to an MHC class II protein, for example, a method wherein step (a) further comprises selecting the heteropolymer that inhibits class 11-specific T cell responses to an MHC class II protein-peptide complex, and a method wherein the antigenic peptide is associated with an autoimmune disease; in another embodiment of the invention, a method is provided wherein the MHC class II protein is associated with an autoimmune disease.

In another embodiment, the method for treating an autoimmune disease in a mammal further involves inhibiting the proliferation or function of T cells which are responsive to an autoantigen. RA is a T cell-mediated autoimmune disease which can be treated with the present polypeptides. The pathological process of autoimmune diseases and immune rejection is mediated by T cells. Upon binding to and recognition of an antigen, T cells proliferate, secrete cytokines and recruit additional inflammatory and cytotoxic cells to the site. The present polypeptides prevent T cell proliferation and T cell functions such as cytokine secretion and recruitment of inflammatory and cytotoxic cells to the site. When the autoimmune disease is an arthritic condition the autoantigen can be collagen, and the present polypeptides can inhibit the proliferation and function of collagen-responsive T cells.

In another embodiment, the method for treating an autoimmune disease in a mammal involves binding the polypeptide to an antigen presenting cell such as a macrophage, a dendritic cell of the lymphoid tissue or an epidermal cell. The proliferation and functions of a T cell are activated when an appropriate antigen is presented to it. By binding to antigen presenting cells, the present polypeptides may block or otherwise interfere with T cell activation.

In yet another embodiment, the method for treating an autoimmune disease in a mammal involves binding the polypeptide to a major histocompatibility complex class II protein which is associated with an autoimmune disease. The Class II MHC proteins are expressed predominantly on the surfaces of B lymphocytes and antigen presenting cells such as macrophages. These Class II MHC proteins have a peptide-binding cleft which is the site at which antigenic peptides are presented to T cells. When the present polypeptides bind to a major histocompatibility complex class II protein, those polypeptides can block or otherwise interfere with antigen presentation and/or T cell activation.

In another embodiment, the method for treating an autoimmune disease in a mammal involves binding the polypeptide to Copolymer 1-reactive B cell antibodies, and/or Copolymer 1-reactive T cells. Copolymer 1-reactive $T_H2/3$ T cells facilitate the therapeutic effects of Copolymer 1. When binding to Copolymer 1-reactive T cells, the present polypeptides stimulate those T cells to proliferate, secrete antiinflammatory cytokines and enhance the therapeutic benefits of treatment by the present methods. According to the present invention, the present polypeptides also bind to autoantigen-reactive antibodies which may block the antibody from attacking the target tissue, thereby helping to prevent the autoimmune disease from progressing. For example, when the present polypeptides are bound to MBP-specific antibodies, those antibodies may not bind to MBP and thereby lead to the destruction of MBP in the myelin sheath. The present polypeptides may be administered by any convenient route. In one embodiment the present polypeptides can be administered by injection to facilitate delivery to the tissues affected by the autoimmune disease. Thus, the present polypeptides may, for example, be injected, ingested, inhaled, or topically applied. The subject polypeptides may be incorporated into a cream, solution or suspension for topical administration. The present polypeptides are preferably administered orally, topically or by injection without addition of an adjuvant.

Useful Kits of the Invention

Another embodiment of the invention, provides a kit for assaying the binding of an analyte to an MHC protein, which includes a water-soluble MHC protein which has been recombinantly produced in a non-mammalian cell, and a means for detection of the bound analyte on the MHC protein, and instructions for use. The MHC protein used in the kit is an MHC class II protein selected from the group consisting of an MHC class II HLA-DR1 protein, an MHC class II HLA-DR2 protein and an MHC class II HLA-DR4 protein. The kit can further comprise an autoantigenic peptide.

In a preferred embodiment, the MHC class II protein is produced in an invertebrate or a microbial cell, such as an insect cell or a yeast cell and is therefore devoid of bound peptide in the antigen cleft. The means for detecting binding of the analyte to the MHC protein can be any radioactive, fluorimetric, chemiluminescent, enzymatic or calorimetric means known to one of ordinary skill in the art. In a preferred embodiment, the MHC protein is a class II HLA-DR1 or HLA-DR4 protein. Further, the kit can include also an autoantigenic peptide, such as a collagen 11 peptide, or a peptide derived from myelin basic protein, myelin oligodendrite protein, or a peptide from some other protein implicated in an autoimmune disease.

Synthesis of the Terpolymers of the Invention

The Terpolymers can be made by any procedure available to one of skill in the art. For example, the Terpolymers can be made under condensation conditions using the desired molar fraction of amino acids in solution or by solid phase synthetic procedures. Condensation conditions include the proper temperature, pH and solvent conditions for condensing the carboxyl group of one amino acid with the amino group of another amino acid to form a peptide bond. Condensing agents, for example, dicyclohexyl-carbodiimide, can be used to facilitate the formation of the peptide bond. Blocking groups can be used to protect functional groups, such as the side chain moieties and some of the amino or carboxyl groups, against undesired side reactions.

For example, the process disclosed in U.S. Pat. No. 3,849,550 can be used where the N-carboxyanhydrides of tyrosine, alanine, γ-benzyl glutamate and N-trifluoroacetyl-lysine are polymerized at ambient temperatures in anhydrous dioxane with diethylamine as an initiator. The γ-carboxyl group of the glutamic acid can be deblocked by hydrogen bromide in glacial acetic acid. The trifluoroacetyl groups are removed from lysine by 1 molar piperidine. One of skill in the art readily understands that the process can be adjusted to make polypeptides containing the desired amino acids, for example, only three of the four amino acids in Copolymer 1 by selectively eliminating the reactions that relate to any one of glutamic acid, alanine, tyrosine or lysine. For purposes of the application, the terms "ambient temperature" and "room temperature" mean a temperature ranging from about 20 to about 26 degrees Centigrade (° C.).

The average molecular weight of the Terpolymers can be adjusted during polypeptide synthesis or after the Terpolymers have been made. To adjust the average molecular weight during polypeptide synthesis, the synthetic conditions or the amounts of amino acids are adjusted so that synthesis stops when the polypeptide reaches the approximate length which is desired. After synthesis, polypeptides with the desired average molecular weight can be obtained by any available size selection procedure, for example, chromatography of the polypeptides on a molecular weight sizing column or gel, and collection of the average molecular weight ranges desired. The present polypeptides can also be partially hydrolyzed to remove high molecular weight species, for example, by acid or enzymatic hydrolysis, and then purified to remove the acid or enzymes.

In one embodiment, the present invention provides a process for preparing Terpolymers with a desired average molecular weight which includes reacting a protected polypeptide with hydrobromic acid to form a polypeptide having the desired average molecular weight profile. The reaction is performed for a time and at a temperature which is predetermined by one or more test reactions. During the test reactions, the time and temperature are varied and the average molecular weight range of a given batch of test polypeptides is determined. The test conditions which provide the optimal average molecular weight range for that batch of polypeptides are used for the batch. Thus, polypeptides having the desired average molecular weight profile, can be produced by a process which includes reacting the protected polypeptide with hydrobromic acid for a time and at a temperature predetermined by test reaction.

In a preferred embodiment, a test sample of protected polypeptide from a given batch is reacted with hydrobromic acid for about 10-50 hours at a temperature of about 20-28° C. The best conditions for that batch are determined by running several test reactions. For example, in one embodiment, the protected polypeptide is reacted with hydrobromic acid for about 17 hours at a temperature of about 26° C.

The examples which follow describe the invention in detail with respect to showing how certain specific representative embodiments thereof can be made, the materials, apparatus and process steps being understood as examples that are intended to be illustrative only. In particular, the invention is not intended to be limited to the methods, materials, conditions, process parameters, apparatus and the like specifically recited herein.

Throughout this application, various publications, patents, and patent applications have been referred to. The teachings and disclosures of these publications, patents, and patent applications in their entireties are hereby incorporated by reference into this application to more fully describe the state of the art to which the present invention pertains.

It is to be understood and expected that variations in the principles of invention herein disclosed may be made by one skilled in the art and it is intended that such modifications are to be included within the scope of the present invention.

EXAMPLE 1

Preparation of Polypeptides

Preparation of Protected Polypeptides

Protected polypeptides are prepared as described by Teitelbaum et al., using the N-carboxyanhydride (NCA) blocked amino acids tyrosine, alanine, glutamic acid and trifluoroacetyllysine dissolved in dioxane. 1 EUR. J. IMMUN. 242 (1971). The carboxylate group on glutamic acid is blocked with a benzyl (BZ) group.

The polymerization process is initiated by the addition of 0.01-0.02% diethylamine. The reaction mixture is stirred at room temperature for 20 hours and then poured into water. The protected polypeptide product is filtered, washed with water and dried. The removal of the γ-benzyl blocking groups from the glutamate residue is carried out by treating the protected polypeptide with 33% hydrobromic acid in glacial acetic acid at room temperature for 6-12 hours with stirring. The product is poured into excess water, filtered, washed and dried, yielding the protected polypeptide.

Preparing Polypeptides with Molecular Weight 7,000±2,000 Da

Treatment of γ-benzyl protected polypeptides 33% HBr in acetic acid not only insures removal of the benzyl protecting group from the γ-carboxylate of the glutamate residue but also cleaves the polypeptides into smaller polypeptides. The time needed for obtaining a polypeptide of molecular weight 7,000±2,000 daltons depends on the reaction temperature and the size of protected polypeptide. At temperatures of between 20° C. to 28° C. a test reaction is performed on every batch for different time periods, for example, from 10-50 hours. A curve of average molecular weight obtained over time is drawn. The time needed for obtaining molecular weight 7,000±2,000 Da is calculated from the curve and the reaction is performed on a larger scale. On average, at 26° C., the time period for obtaining a mixture of polypeptides with a molecular weight of 7,000±2,000 Da is 17 hours. The product is poured into excess water, filtered, washed and dried, yielding a polypeptide with a desired range of average molecular weights.

Preparation of Low-Toxicity Lysine-Containing Polypeptides

Protected trifluoroacetyl-polypeptide (20 g) is dispersed in 1 liter of water and 100 g piperidine is added. The mixture is stirred for 24 hours at room temperature and filtered. The solution of crude polypeptide is distributed into dialysis bags and dialyzed at 10-20° C. in water until pH 8 is attained. The polypeptide solution is dialyzed in 0.3% acetic acid and then again in water until pH 5.5 to 6.0 is obtained. This solution is then concentrated and lyophilized to dryness.

Synthesis of: Molecular Weight 7,600 TGA, poly[L-Tyr$^{0.136}$, L-Glu$^{0.21}$, L-Ala$^{0.648}$]

1) Raw Materials:

| | |
|---|---|
| L-Ala-NCA | 18.74 g |
| L-Tyr-NCA | 6.5 g |
| 5-BZ-L-Glu-NCA | 13 g |
| Diethylamine | 0.165 g |
| Dioxane | 790 ml |
| HBr/AcOH (33%) | 480 ml |
| Phenol | 4.8 g |
| Piperidine | 13.2 ml |
| Deionized water | |
| Acetic acid | |

2) Procedure:

L-Tyr-NCA (6.5 g) is placed in dioxane (211 ml) and heated to 60° C. for 10 min, then filtered. 5-BZ-L-Glu-NCA (13 g) is placed in dioxane (226 ml) and stirred at 20-25° C. for 10 min, then filtered. L-Ala-NCA (18.74 g) is placed in dioxane (350 ml) and stirred at 20-25° C. for 10 min, then filtered.

A 2 L Erlenmeyer equipped with a magnetic stirrer, is charged with the solution of L-Tyr-NCA, the solution of 5-BZ-L-Glu-NCA and the solution of L-Ala-NCA. Diethylamine (0.165 g) in dioxane (2.5 ml) is introduced to the reaction mixture and stirred at 20-25° C. for 20 hours. The reaction mixture is added to deionized water (1 L), filtered and dried at 60° C. under vacuum. Yield –25.8 g.

A solution of phenol (4.8 g) in HBr/AcOH (33%;480 ml) is stirred for 20 hours. A 2 L Erlenmeyer equipped with a magnetic stirrer, is charged with a solution of HBr/AcOH, poly[5-BZ-L-Glu,L-Ala,L-LTyr] and stirred at 26±1° C. for 16 hours. The reaction mixture is added to deionized water (2 L) and stirred for 1 hour. The precipitate is filtered and washed with deionized water until the pH is 6. The product is dried in a circulating air oven at 40° C., for about 40 hours. Yield –24 g.

A 2 L Erlenmeyer equipped with a magnetic stirrer, is charged with a piperidine (13.2 ml), deionized water (1200 ml), and poly[L-Glu,L-Ala,L-LTyr], then stirred at 20-25° C. for 24 hours. The resulting solution is ultrafiltered through polyethersulphone membranes with a cutoff of 5000 daltons until two thirds of the original volume is removed. The original volume is restored by addition of fresh deionized water. The process is repeated 5 times, until the impurity content is less than 1% by HPLC . The resulting solution (at full volume) is acidified to pH 4.4 with acetic acid. The solution is ultrafiltered to pH 5.5-6 and the volume is reduced to one third. The resulting solution is lyophilized to dryness.

Synthesis of Molecular Weight 8850 GAL, poly[L-Glu$^{0.153}$, L-Ala$^{0.479}$, L-Lys$^{0.365}$]

1) Raw Materials

| | |
|---|---|
| L-Ala-NCA | 14 g |
| N6-TFA-L-Lys-NCA | 22.9 g |
| 5-BZ-L-Glu-NCA | 9.8 g |
| Diethylamine | 0.12 g |
| Dioxane | 850 ml |
| HBr/AcOH (33%) | 480 ml |
| Phenol | 4.8 g |
| Piperidine | 13.2 ml |
| Deionized water | |
| Acetic acid | |

2) Procedure

N6-TFA-L-Lys-NCA (22.9 g) in dioxane (420 ml) is stirred at 20-25° C. for 10 min. and filtered. 5-BZ-L-Glu-NCA (9.8 g) in dioxane (170 ml) is stirred at 20-25° C. for 10 min. and filtered. L-Ala-NCA (14 g) in dioxane (260 ml) is stirred at 20-25° C. for 10 min. and filtered. A 2 L Erlenmeyer equipped with a magnetic stirrer, is charged with the solution of N6-TFA-L-Lys-NCA, the solution of 5-BZ-L-Glu-NCA and the solution of L-Ala-NCA. Diethylamine (0.12 g) in dioxane (2.5 ml) is added, and the reaction mixture is stirred at 20-25° C. for 20 hours. The reaction mixture is added to deionized water (1 L), filtered and dried at 60° C. under vacuum.

A solution of phenol (4.8 g) in HBr/AcOH (33%;480 ml) is stirred for 20 hours. A 2 L Erlenmeyer equipped with a magnetic stirrer, is charged with a solution of HBr/AcOH, poly[5-BZ-L-Glu,L-Ala,N6-TFA-L-Lys] (24 g) and is stirred at 26±1° C. for 16 hours. The reaction mixture is added to deionized water (2 L) and stirred for 1 hour. The precipitate is filtered and washed with deionized water until pH=6. The product is dried in a circulating air oven at 40° C., about 40 hours.

A 2 L Erlenmeyer equipped with a magnetic stirrer, is charged with piperidine (13.2 ml), deionized water (1200 ml) and poly[L-Glu, L-Ala,N6-TFA-L-Lys] (24 g) is stirred at 20-25° C. for 24 hours. The solution is ultrafiltered through polyethersulphone membranes with a cut off of 5000 daltons until two thirds of the original volume are removed. The original volume is restored by addition of fresh deionized water. The process is repeated 5 times, until the impurity content is less than 1% (by HPLC). The resulting solution (at full volume) is acidified to pH 4.4 with acetic acid. The solution is ultrafiltered until the pH is 5.5-6 and the volume is reduced to one third. The resulting solution is lyophilized to dryness.

Synthesis of Molecular Weight 11,050 TGL, poly[L-Tyr$^{0.162}$, L-Glu$^{0.259}$, L-Lys$^{0.579}$]

1) Raw Materials

| | |
|---|---|
| 5-BZ-L-Glu-NCA | 10.34 g |
| N6-TFA-L-Lys-NCA | 24.16 g |
| L-Tyr-NCA | 5.2 g |
| Diethylamine | 0.095 g |
| Dioxane | 810 ml |
| HBr/AcOH (33%) | 460 ml |
| Phenol | 4.6 g |
| Piperidine | 150 ml |
| Deionized water | |
| Acetic acid | |

2) Procedure

L-Tyr-NCA (5.2 g) in dioxane (180 ml) is heated to 60° C. for 10 min, and filtered. N6-TFA-L-Lys-NCA (24.16 g) in dioxane (450 ml) is stirred at 20-25° C. for 10 min. and filtered. 5-BZ-L-Glu-NCA (10.35 g) in dioxane (180 ml) is stirred at 20-25° C. for 10 min. and filtered.

A 2 L Erlenmeyer equipped with a magnetic stirrer, is charged with the solution of N6-TFA-L-Lys-NCA, the solution of L-Tyr-NCA and the solution of 5-BZ-L-Glu-NCA. Diethylamine (0.095 g) in dioxane (2.5 ml) is introduced, and the reaction mixture is stirred at 20-25° C. for 20 hours. The reaction mixture is added to deionized water (0.7 L), filtered and dried at 60° C. under vacuum.

A solution of phenol (4.6 g) in HBr/AcOH (33%;460 ml) is stirred for 20 hours. A 2 L Erlenmeyer equipped with a magnetic stirrer, is charged with the solution of HBr/AcOH and the poly[5-BZ-L-Glu,L-Tyr,N6-TFA-L-Lys]. This mixture is stirred at 26±1° C. for 16 hours and then the mixture is added to deionized water (1.5 L) and stirred for ½ hour. The precipitate is filtered and washed with deionized water until the pH is 5.5.

A 2 L Erlenmeyer equipped with a magnetic stirrer, is charged with a piperidine (150 ml), deionized water (1400 ml), and poly[L-Glu,L-Tyr,N6-TFA-L-Lys] (50 g) and is stirred at 20-25° C. for 24 hours. The resulting solution of poly[L-Glu, L-Tyr, L-Lys] is ultrafiltered through polyethersulphone membranes with a cut off of 5000 daltons until two thirds of the original volume were removed. The original volume is restored by addition of fresh deionized water. The process is repeated 5 times, until the impurity content is less than 1% (by HPLC). The resulting solution (at full volume) is acidified to pH 4.2 with acetic acid. The solution is ultrafiltered to a pH of 5.5-6 and the volume is reduced to one third. The resulting solution is lyophilized to dryness.

Synthesis of Molecular Weight 20,000 TAL, poly[L-Tyr$^{0.102}$, L-Ala$^{0.542}$, L-Lys$^{0.353}$]

1) Raw Materials

| | |
|---|---|
| L-Ala-NCA | 14 g |
| N6-TFA-L-Lys-NCA | 22.9 g |
| L-Tyr-NCA | 4.9 g |
| Diethylamine | 0.1 g |
| Dioxane | 850 ml |
| HBr/AcOH (33%) | 500 ml |
| Phenol | 5 g |
| Piperidine | 162 ml |
| Deionized water | |
| Acetic acid | |

2) Procedure

L-Tyr-NCA (4.9 g) in dioxane (170 ml) is heated to 60° C. for 10 min, and filtered. N6-TFA-L-Lys-NCA (22.9 g) in dioxane (417 ml) is stirred at 20-25° C. for 10 min. and filtered. L-Ala-NCA (14 g) in dioxane (260 ml) is stirred at 20-25° C. for 10 min. and filtered.

A 2 L Erlenmeyer equipped with a magnetic stirrer, is charged with the solution of N6-TFA-L-Lys-NCA, the solution of Tyr-NCA in dioxane and the solution of L-Ala-NCA. Diethylamine (0.1 g) in dioxane (2 ml) is introduced and the mixture is stirred at 20-25° C. for 20 hours. The reaction mixture is then added to deionized water (1 L), filtered and dried at 60° C. under vacuum.

A solution of phenol (5 g) in HBr/AcOH (33%;500 ml) is stirred for 20 hours. A 2 L Erlenmeyer equipped with a magnetic stirrer, is charged with the solution of HBr/AcOH and the poly[L-Ala,L-Tyr,N6-TFA-L-Lys] and is stirred at 26±1° C. for 16 hours. The reaction mixture is then added to deionized water (2 L) and stirred for ½ hour. The precipitate is filtered and washed with deionized water until the pH is 5.5.

A 2 L Erlenmeyer equipped with a magnetic stirrer, is charged with a piperidine (162 ml), water (1500 ml) and the poly[L-Ala,L-Tyr,N6-TFA-L-Lys] (30 g), and is stirred at 20-25° C. for 24 hours. The resulting solution of poly[L-Ala,L-Tyr,L-Lys] is ultrafiltered through polyethersulphone membranes with a cut off of 5000 daltons until two thirds of the original volume were removed. The original volume is restored by addition of fresh deionized water. The process is repeated 5 times, until the impurity content is less than 1% (by HPLC). The resulting solution (at full volume) is acidified to pH 4.4 with acetic acid. The solution is ultrafiltered to pH 5.5-6 and the volume is reduced to one third. The resulting solution is lyophilized to dryness.

EXAMPLE 2

Low Molecular Weight Polypeptides

In Vivo Tests

Three batches of copolymer-1 having an average molecular weight of 7.3 and 8.4 KDa (less than 2.5% copolymer-1 species over 40KDa) and 22KDa (more than 5% copolymer-1 species over 40KDa) were subjected to the toxicity test described below. Five mice were used in each experimental group.

Method

Copolymer-1 is dissolved in distilled water to yield a solution of 2 mg/ml of the active ingredient. Each mouse is injected with 0.5 ml of the test solution into the lateral tail vein. Mice were observed for mortality and relevant clinical signs over a 48 hour period. Observations were recorded 10 minutes, 24 hours and 48 hours post-injection. If, at the end of 48 hours, all the animals were alive and no adverse signs had been observed, then the batch is designated "non-toxic". If, however, one or more of the mice had died or had shown adverse signs, then the batch is designated "toxic".

Results

Three of five mice died after 48 hours when treated with the 22 kDa average molecular weight Copolymer 1 polypeptides. Accordingly, this high average molecular weight batch is designated "toxic". The Copolymer 1 batches having average molecular weights of 7.3 and 8.4 KDa were both designated "non-toxic."

In Vitro Rat Basophilic Leukemia Cell Degranulation Tests

Histamine (or serotonin) release from basophile is an in vitro model for immediate hypersensitivity. The Rat Basophilic Leukemia cell line, RBL-2H$_o$, is uniform and easy to maintain in culture but is a highly sensitive and reproducible system for testing for degranulation. E. L. Basumian, et al., 11 EUR. J. IMMUNOL. 317 (1981). The physiological stimulus for histamine release involves binding of the antigen to membrane-bound IgE molecules, which triggers an intricate biochemical cascade. Degranulation is induced by non-IgE-mediated stimuli, including various peptides and synthetic polymers, e.g. polylysine. R. P. Siraganian, TRENDS IN PHARMACOLOGICAL SCIENCES 432 (October 1983). The RBL degranulation test is, therefore, used to screen out those batches of COP-1 which evoke substantial degranulation and thus might elicit undesirable local and/or systemic side effects.

Method

Rat Basophilic Leukemia cells (RBL-2H$_o$), are loaded with [H$^3$]-serotonin, followed by incubation with 100 µg of the COP-1 to be tested. Batches of COP-1 which induce non-specific degranulation, release [H$^3$]-serotonin into the medium. The radioactivity in the medium is counted by a scintillation counter and the total radiolabeled serotonin incorporated into the cells is determined in the pelleted cells. Percent degranulation is calculated as the percentage of serotonin released out of the total incorporated.

Results

Four batches of Copolymer 1, with average molecular weight between 8,250-14,500 were analyzed for both percentage of the species with molecular weight over 40 kDa and for degranulation of RBL's. Results are summarized in Table 1.

TABLE 1

| Average M.W. | % of species with M.W. over 40 KDa | % Serotonin Release |
|---|---|---|
| 6,250 | <2.5 | 12.4 |
| 7,300 | <2.5 | 21.0 |
| 13,000 | >5 | 66.9 |
| 14,500 | >5 | 67.8 |

As can be seen, when the percentage of high average molecular weight species is low (less than 2.5%), the percent release of serotonin is also low, and vice versa. These data indicate that lower average molecular weight Copolymer 1 polypeptides are preferable to higher average molecular weight Copolymer 1 polypeptides.

EXAMPLE 3

Suppression of EAE by the Polypeptides

Injection of Copolymer 1 in incomplete Freund's adjuvant before disease induction can suppress experimental allergic encephalomyelitis (EAE). This suppression appears to be mediated by Copolymer 1-specific suppressor T cells of the T$_H$2 type which cross react with myelin basic protein. Lando et al., 123 J. IMMUNOL. 2156 (1979); Aharoni et al., 17 EUR. J. IMMUNOL. 23 (1993); Aharoni et al., 94 PROC. NATL. ACAD. SCI. USA 10821 (1997). Other researchers have observed that the therapeutic effect of Copolymer 1 in multiple sclerosis patients is also associated with the induction of T$^H$2 cells. Lahat et al., 244 J. Neurol. 129 (1997). In this example, EAE is suppressed to by different polypeptides of the present invention.

Methods

Copolymer 1

Copolymer 1 batches # 02095 and 55495, with average molecular weights of 6000 Da and 5800 Da, respectively, were obtained from Teva Pharmaceutical Industries (Petach Tikva, Israel).

Terpolymers

Four terpolymers were obtained from Teva Pharmaceutical Industries (Petach Tikva, Israel). The properties of these terpolymers are provided below:

1) The GAL terpolymer (SD-1689) is a mixture of polypeptides containing the following mole fraction of amino acids glutamic acid (0.153), alanine (0.479) and lysine (0.365). The range of GAL average molecular weights is about 4650 daltons to about 20,050 daltons. The average molecular weight of this GAL preparation is 8850 daltons.
2) The TGA terpolymer (SD-1690) is a mixture of polypeptides containing the following mole fraction of amino acids tyrosine (0.136), glutamic acid (0.210) and alanine (0.648). The range of TGA average molecular weights is about 1000 daltons to about 40,000 daltons. The average molecular weight of this TGA preparation is 7600 daltons.
3) The TAL terpolymer (SD-1691) is a mixture of polypeptides containing the following mole fraction of amino acids tyrosine (0.102), alanine (0.542) and lysine (0.353). The range of TAL average molecular weights is about 5700 daltons to about 34,400 daltons. The average molecular weight of this TAL preparation is about 20,000 daltons.
4) The GTL terpolymer (SD-1697) is a mixture of polypeptides containing the following mole fraction of amino acids glutamic acid (0.259), tyrosine (0.162) and lysine (0.579). The range of GTL average molecular weights is about 4,000 daltons to about 23,500 daltons. The average molecular weight of this GTL preparation is about 11050 daltons.

A control polypeptide is used, consisting of a mixture of polypeptides containing a 1:1:1 mixture of amino acids alanine, glutamic acid and tyrosine, with an average molecular weight 26,700 Da. This polypeptide is obtained from Sigma Chemical Company (St. Louis, Mo.).

Induction of EAE

Two to three month old female (SJL/J×BALB/c)FI mice are injected in all four footpads with mouse spinal cord homogenate (3.5 mg/mouse) emulsified in a 1:1 ratio in complete Freund's adjuvant (CFA) supplemented with 4 mg/ml H37Ra. Pertussis toxin (0.25 ml, 250ng, Sigma) is injected intravenously, immediately after and 48 hr later. Mice are examined daily from day 10 post induction for clinical signs of EAE which were scored on a 0-5 scale as described in Lando et al., 123 J. IMMUNOL. 2156 (1979).

EAE Suppression by Injection With Incomplete Adjuvant

The tested polypeptides (10 mg/mouse) are injected in incomplete Freund's adjuvant (ICFA) subcutaneously in one nuchal area in 2-3 spots. EAE is induced 3 weeks later as described above.

EAE Suppression by Oral Administration

In a second test, female Lewis rats are fed 5 mg/kg guinea pig BP or Copolymer 1 dissolved in phosphate buffered saline (PBS) at 2-3 day intervals before EAE induction. EAE is induced two days after the last feeding by injection of 25 µg guinea pig MBP emulsified in 1:1 CFA containing 4 mg/ml mycobacterium tuberculosis (H37Ra) (Difco Lab, Detroit, Mich.). A total volume of 0.1 ml is injected into each of two hindfoot pads. Control rats are mock fed with phosphate buffered saline.

The efficacy of orally administered Copolymer 1 for preventing EAE in rats is compared to that of rats fed guinea pig MBP by the method of Higgins et al., 140 J. IMMUNOL. 440 (1988).

Animals were examined daily from day 10 post induction for signs of disease. EAE is scored as follows: 0=no disease; 1=limp tail; 2=hind limb paralysis; 3=paralysis of all four limbs; 4=moribund condition; and 5=death.

Results

EAE Suppression by Injection With Incomplete Adjuvant

Table 2 illustrates the effects of administering the present polypeptides by injection in ICFA prior to induction of EAE. Of the four polypeptides tested, Copolymer 1 and TAL caused the greatest EAE suppression. GTL also exhibited good suppressive activity. GAL and TGA, were somewhat less effective.

TABLE 2

Suppression of EAE in mice by Injection of the Present Polypeptides

| Polypeptide | Incidence | MMS* | Suppression % Incidence | MMS* |
|---|---|---|---|---|
| None (Negative Control) | 11/11 | 4.0 | | |
| ICFA (Negative Control) | 11/11 | 3.4 | 0.0 | 15.0 |
| Copolymer 1 (Positive Control) | 2/11 | 0.45 | 82.0 | 89.0 |
| SD-1689-GAL | 7/8 | 3.5 | 12.5 | 12.5 |
| SD-1690-TGA | 6/8 | 2.5 | 25.0 | 37.5 |
| SD-1691-TAL | 3/8 | 1.1 | 62.5 | 72.5 |
| SD-1697-GTL | 5/8 | 1.5 | 37.5 | 62.5 |
| D-Copolymer 1 | 11/11 | 4.1 | 0.0 | 0.0 |

*MMS = Mean Maximal Score
D-Copolymer 1 is a copolymer of d-lysine, d-tyrosine, d-glutamic acid and d-alanine in the molar ratios of Copolymer 1.

Table 3 illustrates the efficacy of orally administered Copolymer 1 in preventing the clinical manifestations of EAE in Lewis rats compared to rats receiving only phosphate buffered saline (PBS) or guinea pig basic protein (GPBP).

TABLE 3

Suppression of EAE in Rats by Oral Administration of the Present Polypeptides

| Fed Antigen | Incidence | MMS ± SD | Mean Onset (days) |
|---|---|---|---|
| PBS (Control) | 27/28 (96%) | 1.8 ± 0.5 | 11.9 |
| GPBP | 10/17 (59%) p = 0.0026 | 0.9 ± 0.5 | 11.4 |
| Copolymer 1 | 13/28 (46%) p = 0.00005 | 0.78 ± 0.45 | 12.6 |

Each numerical value represents the cumulative results of 3–5 independent experiments. The p values represent the statistical significance of the difference from the control (PBS) group. Mean maximal score is calculated for the entire group.

These data indicate that the present polypeptides are therapeutically effective for preventing the onset and severity of EAE when administered either orally or by injection.

EXAMPLE 4

Binding to Antigen Presenting Cells

Several of the present polypeptides bind efficiently to living antigen presenting cells.

Methods

Copolymer 1

Copolymer 1 batches #02095 and 55495, with average molecular weights of 6000 Da and 5800 Da, respectively, were obtained from Teva Pharmaceutical Industries (Petach Tikva, Israel).

Terpolymers

GAL, TGA, TAL, GTL and control polypeptides are as described above under Example 3.

Biotinylation of Antigens

Biotinylation of Copolymer 1 and Terpolymers is performed at 0° with biotin-N-hydroxysuccinimide (Sigma) according to Fridkis-Hareli et al. 91 PROC. NATL. ACAD. SCI. USA 4872 (1994).

Binding of Biotinylated Antigens to Antigen Presenting Cells

The biotinylated polypeptides were examined for binding to living antigen presenting cells of mouse and human origin, using fluorescently labeled streptavidin and FACS analysis. Adherent spleen cells from (SJL/J×BALB/c)FI mice, or EBV transformed human B cells of DR7,w I I haplotype (1×10$^6$/100 µl), were incubated at 37° C. for 20 hr. with 50 µg biotinylated Copolymer 1 or Terpolymers dissolved in 100 µl PBS containing 0.1% BSA. The cells were then incubated at 4° C. for 30 min. with phycoerythrin-conjugated streptavidin (Jackson Immuno Research, West Grove, Pa.) at a concentration of 0.5 µg/100 µl cell suspension. After each incubation the cells were washed three times with PBS containing 0.1% BSA. Thereafter, cells were analyzed by flow cytometry using FACScan (Becton-Dickinson, Mountain View, Calif.). For each analysis, 5000 cells were examined. Dead cells were excluded on the basis of forward and side-angle light scatter.

Epstein-Barr Virus (EBV) Transformed B-Cell Lines

EBV-transformed B-cell lines were initiated according to Teitelbaum et al., 89 PROC. NATL. ACAD. SCI. USA 137 (1992). Approximately 20×10$^6$ peripheral blood mononuclear cells were cultured with B95.8 cell line supernatant, for 1 hr at 37° C. The cells were then washed and cultured in RPMI medium with 10% FCS and cyclosporin A (10 µg/ml) to deplete T cells.

Results

Table 4 illustrates the binding of terpolymers and Copolymer 1 polypeptides to living antigen presenting cells, including mouse spleen macrophages and human EBV transformed B-cell lines. Data illustrating both the percent of binding and the intensity of cell staining are provided (Table 4 I+II). TAL bound the most efficiently—better even than Copolymer 1. GAL and GTL also bound very well—the same or even somewhat better than Copolymer 1. TGA bound well but somewhat less than Copolymer 1.

TAL bound most efficiently both to spleen macrophages of (SJL/J×BALB/c) F$_1$ mice and to EBV-transformed B cells from a normal DR7.w11 donor, as expressed by the intensity of the binding (Table 4).

TABLE 4

Binding of Terpolymers to antigen presenting cells

| Polypeptide | % Binding | MFI* |
|---|---|---|
| I. Antigen presenting cells from mouse spleen macrophages | | |
| Copolymer 1 (positive control) | 85 | 493 |
| SD-1689-GAL | 88 | 600 |
| SD-1690-TGA | 74 | 39 |
| SD-1691-TAL | 100 | 1929 |
| SD-1697-GTL | 90 | 973 |
| II. Antigen presenting cells from human EBV transformed B-cell line | | |
| Copolymer 1 (positive control) | 96 | 727 |
| SD-1689-GAL | 95 | 661 |
| SD-1690-TGA | 72 | 49 |
| SD-1691-TAL | 100 | 1438 |
| SD-1697-GTL | 97 | 1057 |

*MFI = Mean Fluorescence Intensity

EXAMPLE 5

The Present Polypeptides Bind To Purified Human Leukocyte Antigens (HLA)

This example illustrates that polypeptides of the present invention bind to human B cells and to purified human lymphocyte antigens with high affinity, including the HLA-DR1, HLA-DR2 and HLA-DR4 molecules.

Methods

Cell lines and antibodies

Homozygous EBV-transformed human B lymphocyte lines used for immunoaffinity purification of HLA-DR1, -DR2 and -DR4 molecules were LG-2 (DRB1-*), MGAR (DRB1±1501) and Preiss (DRB-*0401/DRB4-*0101), respectively.

Cells were grown in RPMI 1640 supplemented with 10% FCS, 2 mM glutamine, 50 U/ml penicillin G and 50 µg/ml streptomycin in roller bottles and stored as pellets at −80° C. The anti-DR hybridoma LB3.1 (lgG2b) is grown in serum-free medium (Macrophage-SFM, Gibco BRL). See Gorga et al., 103 CELL. IMMUNOL. 160 (1986).

Protein Purification

Immunoaffinity purification of HLA-DR1, -DR2 and -DR4 molecules is performed, with minor modifications, as previously reported by Gorga et al., 262 J. BIOL. CHEM. 16087 (1987). Briefly, detergent soluble membrane preparations from LG-2, MGAR and Priess cells were passed at a flow rate of approximately 11 ml/hr through a series of columns in the following sequence: Sepharose CL-6B (30 ml), normal mouse serum-Aff-gel 10 (10 ml), protein A-Sepharose CL-4B (5 ml) and LB3.1-protein A-Sepharose CL-4B (5 ml). DR2a (DRB5*0101) and Drw53 (DRB4*0101), the products of DR genes linked to the DRB1 alleles were not removed from the MGAR and Priess lysates before passage through the LB3.1 immunoaffinity column, and contaminate the DR2 and DR4 preparations in the amount of 5-10%. All the subsequent steps were as previously described by Gorga et al., 262 J. BIOL. CHEM. 16087 (1987). The eluate is dialyzed against 0.1% deoxycholate, 10 mM Tris-HCl, pH 8.0 and concentrated on a Centriprep 30 membrane (Amicon). Protein concentrations were determined by bicinchonitric acid assay (Pierce Chemical Co.).

Polypeptides and Control Antigens
  Copolymer 1
    Copolymer 1 batches # 55495 and 52596, with average molecular weight of 5800 daltons and 8,150 daltons, respectively, were obtained from Teva Pharmaceutical Industries (Petach Tikva, Israel). Copolymer 1 batch 52596 had a molar ratio of 1 tyrosine: 1.5 glutamic acid: 4.3 alanine: 3.1 lysine.
  Myelin Basic Protein and Hemagglutinin Control Peptides
    MBP peptides were synthesized on an Applied Biosystems Peptide Synthesizer using solid phase techniques. Barany et al., THE PEPTIDES 1 (1979). Peptides purified by reversed-phase HPLC. The peptides used were HA 306-318, having the sequence PKYVKQNTLKLAT (MW 1718) (SEQ ID NO: 2), and MBP 84 102, having the sequence DENPWHFFKNIVTPRTPP (MW 2529) (SEQ ID NO: 1).
  Terpolymers
    GAL, TGA, TAL, GTL and control polypeptides are as described above under Example 3.
Polypeptide Labeling
  Biotinylation of the various polypeptides is performed as in Example 4. Unreacted biotin is removed by dialysis (Spectra/Por® membrane MWCO 500, Spectrum Medical Industries).
Assays for Polypeptide Binding to Class II MHC Proteins
  Solutions: The solutions used in this assay were the following. Binding buffer is 20 mM 2-[N-morpholino] ethanesulfonic acid (MES), 1% n-octyl β-D-glycopyranoside, 140 mM NaCl, 0.05% $NaN_3$, pH 5.0, unless otherwise specified. PBS is 150 mM sodium chloride, 7.5 mM sodium phosphate, dibasic, 2.5 mM sodium phosphate, monobasic, pH 7.2. TBS is 137 mM sodium chloride, 25 mM Tris pH 8.0, 2.7 mM potassium chloride. TTBS is TBS plus 0.05% Tween-20.
  Microtiter Assay Plate Preparation: Ninety-six well microtiter immunoassay plates (PRO-BIND™, Falcon) were coated with 1 μg/well affinity-purified LB3.1 monoclonal antibodies in PBS (100 μl total) for 18 hrs at 4° C. The wells were then blocked with TBS containing 3% BSA for 1 hr at 37° C. and washed three times with TTBS. Before sample addition, 50 μl of TBS/1% BSA is added to each well.
  Binding reactions: Detergent-solubilized HLA-DR1, -DR2 and -DR4 molecules (0.5 μg/sample) were incubated with biotinylated control peptides at various concentrations for 40 hours at 37° C. in 50 μl of the binding buffer and transferred to prepared microtiter assay plates and incubated for 1 hr at 37° C. for capture of polypeptide-class II complexes.
  Inhibition reactions: Biotinylated polypeptides at a final concentration of 1.5 μM in 50 μl of binding buffer were coincubated with unlabeled polypeptides as well as the peptides HA 306-318 (SEQ ID NO: 2) or MBP 84-102 (SEQ ID NO: 1), used as inhibitors, and HLA-DR molecules for 40 hr at 37° C.
  Detection of class II/polypeptide complexes: Bound polypeptide-biotin is detected using streptavidin-conjugated alkaline phosphatase as follows. Plates were washed three times with TTBS and incubated with 100 μl of streptavidin-conjugated alkaline phosphatase (1:3000, BioRad) for 1 hr at 37° C., followed by addition of p-nitrophenyl phosphate in triethanolamine buffer (BioRad). The absorbency at 410 nm is monitored by a microplate reader (Dynatech MR4000).

Results
  Terpolymers Binding to Class II MHC Proteins
    Detergent-soluble HLA-DR1, HLA-DR2 and HLA-DR4 proteins were purified from homozygous EBV-transformed B cell lines LG-2 (DRB1*0101), MGAR (DRB1*1501) and Priess (DRB1*0401), respectively, as described previously by Fridkis-Hareli et al., 160 J. IMMUNOL. 4386 (1998). Three different preparations of Copolymer 1 had bound to these molecules with high affinity. Id. To determine the affinity of the terpolymers for HLA-DR proteins, binding assays were carried out with biotinylated Terpolymers, and compared to Copolymer 1. The polypeptides were incubated at a range of concentrations with purified HLA-DR1, HLA-DR2 and HLA-DR4 molecules at pH 5.0 followed by capture with class II-specific mAb and detection with alkaline phosphatase-streptavidin.
    Binding by TAL and Copolymer 1 to detergent-soluble HLA-DR1 and HLA-DR4 molecules is better than that of GAL, TGA or GTL. However, GTL and Copolymer 1 bound better than the other polypeptides to HLA-DR2, based on the saturation binding curves (FIG. 2A), and on $K_d$ values, calculated from the double-reciprocal plots of the binding data (FIG. 2B, Table 5).
    Competitive binding assays were carried out with biotinylated Copolymer 1 and the following unlabeled inhibitors: Copolymer 1, TAL, TGA, GAL, TGL, MBP 84-102 and HA 306-318 polypeptides (FIG. 3). The MBP 84-102 (SEQ ID NO: 1) peptide is a poor inhibitor of the binding of Copolymer 1 to HLA-DR2. The binding of biotinylated Copolymer 1 to detergent-soluble HLA-DR1 and -DR4 molecules is efficiently inhibited by unlabeled TGA, TAL, HA 306-318 (SEQ ID NO: 2) and Copolymer 1. However, binding of biotinylated Copolymer 1 to detergent-soluble HLA-DR1 and -DR4 molecules is inhibited more than 10-fold less by TGL, as indicated by 50% inhibitory dosages ($IC_{50}$) (FIG. 3, Table 5). Similarly, GAL is also a poor inhibitor of Copolymer 1 binding to HLA-DR1 and -DR4 molecules. In general, the binding pattern to HLA-DR2 is similar to that observed for HLA-DR1 (Table 5). These results show that the polypeptides of three amino acids, in particular TAL and TGA bind to class II MHC molecules with an affinity range similar to that of antigenic peptides and of Copolymer 1. Hence, TAL and TGA are effective competitors for the class II MHC molecules to which Copolymer 1 binds. Based on their binding capacity, the polypeptides could be arranged in the following order:
    (A) binding to HLA-DR1: Copolymer 1>TAL>GTL>TGA>>GAL;
    (B) binding to HLA-DR2: Copolymer 1>GTL>TAL>GAL>TGA;
    (C) binding to HLA-DR4: TAL>Copolymer 1>>TGA>GTL>GAL.

TABLE 5

Affinity of the present polypeptides for purified human HLA-DR1, -DR2 and -DR4 molecules

| Polypeptide[1] | DR1[2] | | DR2 | | DR4 | |
|---|---|---|---|---|---|---|
| | $K_d$[3] | $IC_{50}$[4] | $K_d$ | $IC_{50}$ | $K_d$ | $IC_{50}$ |
| Copolymer 1 | 7.4 | 8.8 | 8.2 | 10.1 | 1.5 | 10.8 |
| TAL | 2.0 | 3.3 | 1.7 | 2.7 | 2.0 | 6.5 |
| GAL | 0.5 | 5 | 1.7 | 5 | 0.3 | 5 |

TABLE 5-continued

Affinity of the present polypeptides
for purified human HLA-DR1, -DR2 and -DR4 molecules

| Polypeptide[1] | DR1[2] | | DR2 | | DR4 | |
|---|---|---|---|---|---|---|
| | $K_d$[3] | $IC_{50}$[4] | $K_d$ | $IC_{50}$ | $K_d$ | $IC_{50}$ |
| TGA | 1.0 | 1.3 | 0.8 | 9.5 | 0.8 | 1.0 |
| TGL | 0.4 | 43.0 | 5.0 | 25.4 | 0.8 | 43.0 |

[1]Copolymer 1 polypeptides with average MW of 5,800; TAL, MW 20,000; GAL, MW 8,850; TGA, MW 7,600; and TGL, MW 11,050, were incubated at a range of concentrations with purified HLA-DR1, -DR2 and -DR4 molecules at pH 5.0 followed by capture with class II-specific mAb and peptide detection with alkaline phosphatase-streptavidin.
[2]Detergent-soluble HLA-DR1, -DR2 and -DR4 molecules were purified as described in Materials and Methods.
[3]$K_d$, the dissociation constant at equilibrium, is calculated from the slope of the double reciprocal plot (FIG. 2B), and is expressed as $\times 10^{-8}$ M.
[4]$IC_{50}$, inhibitory concentration giving 50% inhibition, is calculated based on the competitive binding assays (FIG. 3), and is expressed as $\times 10^{-6}$ M.
[5]$IC_{50}$ values for GAL could not be determined exactly, but were less than 1000 μM (see FIG. 3).

Effect of Superantigens on the Binding of Polypeptides to HLA-DR Molecules

Bacterial superantigens SEA, SEB and TSST-1 have been shown to inhibit Copolymer 1 binding to purified HLA-DR molecules only at very high concentrations. Fridkis-Hareli et al., 160 J. IMMUNOL. 4386 (1998). To examine the effect of these superantigens on the binding of Terpolymers to purified HLA-DR1, HLA-DR2 and HLA-DR4 molecules, competitive binding assays were carried out with unlabeled SEA, SEB and TSST-1.

Binding of TAL to HLA-DR1, HLA-DR2 and HLA-DR4 is only inhibited by the superantigens at high molar ratios of superantigen: for example, fifty times the amount of superantigen is needed to inhibit TAL binding (FIG. 4A). However, binding of TGA and GAL is inhibited more significantly by the superantigens (FIG. 4B and C), indicating that these polypeptides bound the HLA antigens with lower affinity.

EXAMPLE 6

Inhibition of MBP-Induced T Cell Proliferation

This example illustrates that the proliferation of T cells which are normally activated by myelin basic protein (MBP) can be inhibited by simultaneous exposure to the present polypeptides.

Methods

Copolymer 1

Copolymer 1 batches # 02095 and 55495, with average molecular weights of 6000 Da and 5800 Da, respectively, were obtained from Teva Pharmaceutical Industries (Petach Tikva, Israel).

Myelin Basic Protein Peptides were synthesized on an Applied Biosystems Peptide Synthesizer using solid phase techniques. Barany et al., THE PEPTIDES 1 (1979). Peptides purified by reversed-phase HPLC. The peptides used were HA 306-318, having the sequence PKYVKQNTLKLAT (MW 1718)(SEQ ID NO: 2), and MBP 84 102, having the sequence DENPWHFFKNIVTPRTPP (MW 2529) (SEQ ID NO: 1).

Terpolymers

GAL, TGA, TAL, GTL and control polypeptides are as described above under Example 3.

T Cell Lines and Clones

Myelin Basic Protein (MBP) specific T-cell lines originated from spleens of mice which, ten days earlier, were immunized with 20 μg of the 84-102 peptide of MBP emulsified in complete Freund's adjuvant supplemented with 4 mg/ml of Mycobacterium tuberculosis H37Ra. Cells were cultured and selected in vitro using the immunizing antigen (0.2-1 mg/plate), in culture medium (RPMI, 2 mM glutamine, 1 mM sodium pyruvate, non essential amino acids, $5 \times 10^{-5}$ M 2-mercaptoethanol, 100 μg/ml penicillin, 100 μg/ml streptomycin), supplemented with 1% autologous serum. After 4 days, cells were transferred to culture medium containing 10% FCS and supplemented with 10% supernatant of Con A activated normal spleen cells as T cell growth factor (TCGF). Every fourteen to twenty one days, cells were stimulated by exposure to the immunizing antigen presented on syngeneic irradiated (3000 rad) spleen cells ($50 \times 10^6$/plate) for 3 days, followed by propagation in TCGF medium. Cloning of T cell lines is performed by limiting dilution at 0.3 cells/well in microliter plate in the presence of the antigen (2-10 μg/well) and irradiated syngeneic spleen cells ($5 \times 10^6$/well).

Human T cell lines were derived from peripheral blood mononuclear cells according to Teitelbaum et al., 89 PROC. NATL. ACAD. SCI. USA 137 (1992). Approximately $5 \times 10^6$ cells were incubated in each well of a 24-well culture plate with Copolymer 1 or MBP (50 μg/ml) in culture medium supplemented with 10% heat-inactivated autologous serum. After 7 days of culture, the cells were transferred to culture medium containing 10% fetal calf serum and recombinant human interleukin 2 (20 units/ml). The cells were grown continuously in this medium with periodic exposure to antigen presented on irradiated (3000 rad), autologous mononuclear cells, every 14-18 days.

Proliferation Assay

Cells of T lines or clones were tested for their specific proliferative response 10-21 days after antigenic stimulation. T Cells ($1.5 \times 10^4$) were cultured in triplicates with $5 \times 10^5$ irradiated spleen cells and with the indicated antigens in a final volume of 0.2 ml in 10% FCS culture medium. At the end of 48 hr incubation, cultures were pulsed with 1 μCi[$^3$H]-thymidine (standard deviation <20% of the mean cpm), and harvested 6-12 h later.

Inhibition Studies

Inhibition of the T-cell proliferative response is studied by adding various concentrations of Copolymer 1 and Terpolymers plus the stimulating MBP antigen to the proliferation assay system. Inhibition is calculated as percent inhibition using equation 2:

% Inhibition=[1−(cpm with inhibitor/cpm without inhibitor)]×100.  2

Results

FIG. 1 illustrates how copolymer 1 and terpolymers effect the proliferation of T cells which are specific for certain myelin basic protein (MBP) peptides. In general, T cells proliferate when exposed to the antigen to which they were sensitized. Thus, MBP and, in particular, certain antigenic peptides from MBP stimulate the proliferation of MBP-specific T cells.

Copolymer 1 and Terpolymers did not stimulate proliferation of T cells which were specific for the 84-102 peptide of MBP. Instead, they significantly inhibited the proliferation of T cells exposed to this MBP antigen.

TAL exhibited the most efficient inhibition of proliferation in T cells specific for the MBP 84-102 antigen. Inhibition by TAL is even greater than that provided by Copolymer 1. TGA induced lower inhibition of T cell proliferation. GAL and GTL inhibited T cell proliferation in a dose responsive manner similar to Copolymer 1.

EXAMPLE 7

Terpolymers Are Recognized By Some Copolymer 1-Specific T Cells

Terpolymers can stimulate some Copolymer 1-specific T cell lines to proliferate and secrete the cytokine, IL-4.

Methods

Copolymer 1

Copolymer 1 batches # 02095 and 55495, with average molecular weight of 6000 Da and 5800 Da, respectively, were obtained from Teva Pharmaceutical Industries (Petach Tikva, Israel).

Myelin Basic Protein Peptides were synthesized on an Applied Biosystems Peptide Synthesizer using solid phase techniques. Barany et al., THE PEPTIDES 1 (1979). Peptides purified by reversed-phase HPLC. The peptides used were HA 306-318, having the sequence PKYVKQNTLKLAT (MW 1718) (SEQ ID NO: 2), and MBP 84 102, having the sequence DENPWHFFKNIVTPRTPP (MW 2529) (SEQ ID NO: 1).

Terpolymers

GAL, TGA, TAL, GTL and control polypeptides are as described above under Example 3.

T Cell Lines and Clones

Mouse T cell lines and clones were established according to Aharoni et al., 23 Eur. J. Immunol. 17 (1993); Aharoni et al., 94 PROC. NATL. ACAD. SCI. USA 10821 (1997). Copolymer 1 specific lines were originated from spleens of mice which, 15 to 35 days earlier, had been rendered unresponsive to EAE by subcutaneously injecting each mouse with 5-10 mg Copolymer 1, emulsified in incomplete Freund's adjuvant (Difco). Alternatively, Copolymer 1 specific lines were obtained from the lymph nodes of mice which had been immunized ten days earlier with 200 μg Copolymer 1 emulsified in complete Freund's adjuvant (Difco) supplemented with 4 mg/ml of Mycobacterium tuberculosis H37Ra (Difco).

Copolymer 1-specific T cell lines were used and T cell clones LN-1, LN-2, S-3, 5-22-5, C-14, and C-52. The LN-2 antibodies were derived from lymph nodes of (SJL/JxBALB/c) $F_1$ mice injected with Copolymer 1 in CFA. The 5-22-5 antibodies were obtained from spleens of (SJL/JxBALB/C) $F_1$ mice injected with Copolymer 1 in CFA, according to Aharoni et al., 23 EUR. J. IMMUNOL. 17 (1993); Aharoni et al., PROC. NATL. ACAD. SCI. USA 10821 (1997).

Human T cell clones were derived from peripheral blood mononuclear cells according Teitelbaum et al., 89 PROC. NATL. ACAD. SCI. USA 137 (1992). Approximately $5 \times 10^6$ cells were incubated in each well of a 24-well culture plate with Copolymer 1 or MBP (50 μg/ml) in culture medium supplemented with 10% heat-inactivated autologous serum. After 7 days of culture, the cells were transferred to culture medium containing 10% fetal calf serum and recombinant human interleukin 2 (20 units/ml). The cells were grown continuously in this medium with periodic exposure to antigen presented on irradiated (3000 rad), autologous mononuclear cells, every 14-18 days. The C-52 T-cell clone was derived from a DR7,w11 donor, also according to Teitelbaum et al., 89 PROC. NATL. ACAD. SCI. USA 137 (1992).

Proliferation Assay

Cells of T lines or clones were tested for their specific proliferative response 10-21 days after antigenic stimulation. T Cells ($1.5 \times 10^4$) were cultured in triplicates with $5 \times 10^5$ irradiated spleen cells or with human EBV-transformed B cells ($5 \times 10^4$), and with the indicated antigens in a final volume of 0.2 ml in 10% FCS culture medium. At the end of 48 hr incubation, cultures were pulsed with 1 μCi [$^3$H]-thymidine and then harvested 6-12 hr later. The variations of triplicates from their mean were under 20%. cell line cross-reacted only with TAL. No cell lines cross reacted with GTL or with AGT (1:1:1) which has the same amino acids as TGA but in a different mole fraction than TGA or Copolymer 1.

TABLE 6

Cross reactivity of Terpolymers with Copolymer 1 for Copolymer 1 specific T-cell lines and clones
I. Murine T-cell lines and clones

| | Cross reactivity with Copolymer 1 (%) | | | | | | | |
|---|---|---|---|---|---|---|---|---|
| T-cells | LN-3 | | S-3 | | LN-1 | | S-22-5 | |
| Polypeptide | prol* | IL-4‡ | prol* | IL-4‡ | prol* | IL-4‡ | prol* | IL-4‡ |
| SD-1689-GAL | 130 | 139 | 49 | 11 | 0 | 1 | 0 | 0 |
| SD-1690-TGA | 3 | 6 | 102 | 107 | 0 | 1 | 0 | 0 |
| SD-1691-TAL | 3 | 7 | 2 | 3 | 64 | 120 | 0 | 0 |
| SD-1697-GTL | 2 | 4 | 12 | 6 | 0 | 1 | 0 | 0 |
| 1:1:1 AGT | 2 | 0 | 2 | 2 | 1 | 0 | 2 | 0T |

*prol = as measured by proliferation. ‡IL-4 = as measured by Interleukin-4.

| | II. Human T-cell Clones | |
|---|---|---|
| | Cross reactivity with Copolymer 1 (%) | |
| T-cells Polypeptide | C-14 proliferation | C-52 proliferation |
| SD-1689-GAL | 4 | 75 |
| SD-1690-TGA | 1 | 58 |
| SD-1691-TAL | 0 | 0 |
| SD-1697-GTL | 0 | 5 |

EXAMPLE 8

Terpolymers Cross-React with Anti Copolymer 1 Antibodies

Antibodies directed against Copolymer 1 cross-react with Terpolymers which lack either tyrosine, glutamic acid or alanine. However, Terpolymers lacking lysine are not recognized efficiently by anti-Copolymer 1 antibodies.

Antibodies

Mouse anti-MBP and anti-Copolymer 1 monoclonal antibodies were obtained by fusion of MBP- or Copolymer 1-immunized spleen cells from SJL/J mice, with the NSO/1 murine plasmacytoma cell line. Teitelbaum et al., Proc. Natl. Acad. Sci. USA 9528 (1991).

Radioimmunoassay

Flexible plastic microtiter plates were coated with Copolymer 1 or Terpolymers (2 µg/ml). After 16 hr incubation at room temperature, plates were washed three times and saturated for 2 hr with PBS containing 2% bovine serum albumin, 5 0.05% Tween 20, 0.1% sodium azide, 10 mM EDTA, and heparin at 5 units/ml ("PBS buffer"). Monoclonal antibody supernatants (50 µl), were added to the wells for a 2 hr incubation, and the wells were washed again with PBS buffer. $^{120}$I-labeled goat anti-mouse Fab antibodies ($1 \times 10^5$ cpm/well) were added for overnight incubation at 4° C. After extensive washing, radioactivity is measured in a gamma counter.

Methods

ELISA Assay for Antibody Cross-Reactivity

A standard ELISA assay is employed using anti-Copolymer 1 polyclonal antibodies and microtiter plates coated with 2 µg/ml of terpolymer preparation.

Copolymer 1

Copolymer 1 with the following amino acid composition is obtained from Teva Pharmaceutical Industries (Petach Tikva, Israel).

| Amino Acid | Molar Fraction |
| --- | --- |
| L-glutamic acid | 0.141 |
| L-alanine | 0.427 |
| L-tyrosine | 0.095 |
| L-lysine | 0.338 |

Terpolymers

The four Terpolymers of Example 1 were used.

Results

Table 7 indicated that anti-Copolymer 1 polyclonal antibodies cross react with Terpolymers which lack either tyrosine, glutamic acid or alanine. The relatively high percentage binding of the terpolymers lacking glutamic acid (TAL) might be explained by its high average molecular weight. Terpolymers which lack lysine are not efficiently recognized by anti-Copolymer 1 antibodies. These data suggest that charged amino acids like lysine may play a role in the recognition and binding of Copolymer 1 and Terpolymers.

TABLE 7

| Terpolymers | MW* | Percent Binding in separate experiments | | | | Mean | S.D. |
| --- | --- | --- | --- | --- | --- | --- | --- |
| | | 1 | 2 | 3 | 3 | | |
| TAL | 20,000 | 111.1 | 130.1 | 115.8 | 114.0 | 117.8 | 8.48 |
| GAL | 8,850 | 7.5 | 10.8 | 9.3 | 9.2 | 9.2 | 1.35 |
| GTL | 11,050 | 98.7 | 87.0 | n.d.‡ | n.d.‡ | 92.9 | 8.30 |
| TGA | 7,600 | 87.9 | 79.3 | n.d.‡ | n.d.‡ | 83.6 | 6.12 |

*daltons. ‡n.d. - not determined.

Cross Reactivity of Terpolymers with Copolymer 1—Reactive Monoclonal Antibodies

The cross reactivity of the Terpolymers with Copolymer 1 at the level of B cell response is tested using monoclonal antibodies (mAbs), that are either reactive with both Copolymer 1 and MBP (mAbs 2-2-18 and 3-1-45), or are reactive with only Copolymer 1 (mAbs 3-3-9 and 5-7-2). See Teitelbaum et al., 88 Proc. Natl. Acad. Sci. USA 9528 (1991).

Table 8 illustrates that the Terpolymers differed in their ability to bind these mAbs. TGA and GTL were not recognized by any of the Copolymer 1 specific mAbs. On the other hand, TAL and GAL bound to Copolymer 1 and MBP specific mAbs with an affinity which is similar to that of Copolymer 1. GAL and TAL differed only in the binding to one mAb i.e. 5-7-2 which bound to TAL and not to GAL.

TABLE 8

Cross reactivity of Terpolymers with MBP- and Copolymer 1-reactive B cell antibodies

| Antibody | Cross reactivity with Copolymer 1 (%) | | | |
| --- | --- | --- | --- | --- |
| Polypeptide | 2-2-18 | 3-1-45 | 3-3-9 | 5-7-2 |
| SD-1689-GAL | 96 | 98 | 107 | 10 |
| SD-1690-TGA | 3 | 2 | 1 | 10 |
| SD-1691-TAL | 96 | 98 | 103 | 106 |
| SD-1697-GTL | 1 | 2 | 1 | 1 |

2-2-18 is anti mouse MBP monoclonal antibody cross reactive with Copolymer 1
3-1-45 is anti Copolymer 1 monoclonal antibody cross reactive with MBP
3-3-9 is anti Copolymer 1 monoclonal antibody non cross reactive with MBP
5-7-2 is anti Copolymer 1 monoclonal antibody non cross reactive with MBP

EXAMPLE 9

Copolymer 1 and Terpolymers Compete With Collagen for Binding to Human Leukocyte Antigens and Inhibit Collagen-Specific T-Cell Response This example illustrates that Copolymer 1, TAL, GAL, GTL, and TGA compete for binding to MHC proteins with the rheumatoid arthritis-associated immunodominant collagen antigen, CII 261-273 (SEQ ID NO: 3).

Methods

Protein Expression and Purification

Recombinant HLA-DR1 and HLA-DR4 molecules (encoded by DRA/DRB I *0101 and *0401, respectively) were expressed in *Drosophila* S2 cells as described in Stern, L. et al. 68 CELL 465 (1992) and Dessen, A. et al. 7 IMMUNITY 473 (1997). Cells were grown in roller bottles at 26° C. in Excell 401 medium (Sigma, St. Louis, Mo.) supplemented with 0-5% fetal bovine serum (Sigma). Cells were induced by addition of $CuSO_4$ to 1 mM final concentration, then incubated an additional 4-5 days. Immunoaffinity purification of recombinant HLA-DR1 and HLA-DR4 is performed as previously reported by Stern, L. et al. 68 CELL 465 (1992) and Dessen, A. et al. 7 IMMUNITY 473 (1997). Supernatant from harvested cells is sequentially passed through Protein A, Protein G and Protein A-LB3.1 columns, followed by elution of the bound HLA-DR with 50 mM 3cyclohexylamino-1-propane sulfonic acid (CAPS), pH 11.5, and neutralized with 200 mm phosphate (pH 6.0). The eluate is concentrated on a Centriprep 10 membrane (Amicon). Protein concentrations were determined by bicinchoninic acid assay (Pierce Chemical Co.).

Polypeptide Labeling

The present polypeptides and the HA 306-318 peptide were biotinylated as in Examples 4 and 7.

Class II MHC Protein Binding Assay

In this assay, water-soluble recombinantly-produced proteins were incubated with biotinylated polypeptides of the present invention and varying quantities of unlabeled competitor polypeptides, collagen CII peptides or influenza virus HA peptides. Assays were performed in 96-well microliter immunoassay plates (PRO-BOND™, Falcon) which were coated with affinity-purified LB3.1 monoclonal antibodies. Antibody coating is performed by placing 100 µl of 10.0 µg/ml LB3.1 monoclonal antibodies in each well and incubating at 4° C. for 18 hrs. Microtiter wells were then blocked with Tris buffered saline (TBS) containing 3% bovine serum albumin (BSA) for 1 hr at 37° C. and washed three times with TTBS. Before sample addition, 50 µl of TBS containing 1% BSA is added to each well. Phosphate buffered saline (PBS) is 150 mM sodium chloride, 7.5 mM sodium phosphate dibasic, 2.5 mM sodium phosphate monobasic, pH 7.2. Tris buffered saline (TBS) is 137 mM sodium chloride, 25 mM TRIS pH 8.0, 2.7 mM potassium chloride. TTBS is TBS with 0.05% Tween-2G. Other solutions used in this assay are described in Fridkis-Hareli, M. et al., 160 J. IMMUNOL. 4386 (1998).

Binding analysis is performed by incubating the water soluble DR molecules with biotinylated polypeptides of the present invention and varying concentrations of unlabeled inhibitors (Copolymer 1, TAL, GAL, GTL, TGA, Collagen CII 261-273 peptide or HA 306-318 peptide). The collagen type CII peptide 261-273, has SEQ ID NO: 3 (AG-FKGEQGPKGEP) and a molecular weight of 1516. The concentration of DR employed is 0.15 µM. The final concentration of biotinylated Copolymer 1 or terpolymers is 1.5 µM. Incubation is for 40 hr at 37° C. in 50 µl binding buffer at pH 5.0.

Bound label is detected using streptavidin-conjugated alkaline phosphatase as follows. Plates were washed three times with TTBS and incubated with 100 µl of streptavidin-conjugated alkaline phosphatase (1:3000, BioRad, Richmond, Va.) for 1 hr at 37° C., followed by addition of p-nitrophenyl phosphate in triethanolamine buffer (BioRad). The absorbency at 410 nm is monitored by a microplate reader (model MR4000, Dynatech, Chantilly, Va.).

T Cell Hybridoma and Antigen Presenting Cell (APC) Binding Assays

Copolymer 1 and Terpolymers were tested to ascertain if they could inhibit activation of T cells responsive to the collagen CII peptide. Mouse DR1-restricted 3.19 and 19.3 T cell hybridomas and mouse DR4-restricted 3838 and D3 T cell hybridomas were used. Rosloniec, E. F., et al., 185 J. EXP. MED. 1113-1122 (1997); Andersson, E. C., et al., PROC. NATL. ACAD. SCI. USA (1998). Antigen presenting cells (APCs) were L cells transfected with DR1 (the L57.23 cell line provided by Rosloniec, E. F., et al., 185 J. Exp. Med. 1113-1122 (1997)), L cells transfected with DR4, and Priess cells (DRB1*0401/DRB4*0101). T cell stimulation experiments were performed in 96-well microliter plates in a total volume of 0.2 ml. Irradiated (3000-rad) APC ($2.5 \times 10^4$/well) were coincubated with CII 261-273 (40 µg/ml) and varying concentrations of the present polypeptides for 2 hr at 37° C., then T cells ($5 \times 10^4$/well) were added and the incubation is continued for 24 hr at 37° C. Supernatants (30 µl) were removed and incubated with IL-2 dependent CTL-L ($5 \times 10^4$/well) for 12 hr, followed by labeling with $^3$H-thymidine (1 µCi/well) for 12 hr. Plates were harvested and the radioactivity is monitored using a 1450 microbeta Plus liquid scintillation counter (Wallac, Gaithersburg, Md.).

Results

Class II MHC Protein Binding Assay

The recombinant water-soluble HLA-DR1 and -DR4 proteins produced in insect cells were largely free of bound autoantigens or other peptides. Hence, data obtained from insect cell produced proteins can more accurately indicate the actual binding affinities for polypeptides. Fridkis-Hareli et al., 160 J. IMMUNOL. 4386 (1998) (the entire contents of which are hereby incorporated herein by reference).

Competitive binding of each of the Copolymer 1 and Terpolymers to HLA-DR1, HLA-DR2 and HLA-DR4 molecules is depicted in FIG. 5. Binding of each of the Copolymer 1 (YEAK, top panel FIG. 5A) and Terpolymers is substantially greater than that of the CII 261-273 (SEQ ID NO: 3) peptide, as judged by quantity of CII 261-273 (SEQ ID NO: 3) peptide required for 50% inhibition. As also observed above, TAL bound HLA-DR1 and HLA-DR4 with greater affinity than did Copolymer 1. The kinetics of inhibition by unlabeled TAL (YAK, bottom panel FIG. 5A) polypeptides were also somewhat superior to that of the influenza virus peptide HA 306-318 (SEQ ID NO: 2). However, the influenza virus peptide HA 306-318 inhibited the binding of Copolymer 1 and of Terpolymers more efficiently than the CII 261-273 peptide.

T Cell Hybridoma and Antigen Presenting Cell Binding Assay Results

Copolymer 1 and Terpolymers also inhibited DR1-restricted T cell activation by CII collagen peptide (FIG. 6). T cell activation was detected by observing IL-2 production by DR1-restricted-CII-specific T cell hybridomas. Collagen peptide CII 261-273 (SEQ ID NO: 3) at varying concentrations was coincubated with one of the present polypeptides and then T cells (clone 3.19 or 19.3 as indicated) were added, and the mixtures were further incubated. The supernatants from these incubated cells are removed, and were assayed for IL-2 by observing whether the supernatant induced proliferation of IL-2-dependent cytotoxic T lymphocytes (CTL-L). The extent of inhibition by TAL is shown as solid circles (●), by TGA as solid triangles (▲), by GTL as open triangles (∆), and by Copolymer 1 as solid squares (■). Percent inhibition of CTL-L proliferation shown on the ordinate was calculated using equation 1.

Again, TAL is the most potent inhibitor. However, GTL and Copolymer 1 were also potent inhibitors of T cell activation by the CII collagen peptide. TGA inhibited activation less efficiently. Similar results were obtained with other batches of Copolymer 1 and Terpolymers.

A similar inhibition of activation of DR4-restricted T cells was observed, as shown in FIG. 7. IL-2 production was used to assess activation of DR4-restricted CII-specific T cell hybridomas (3838 and D3). The presence of different polypeptides inhibited IL-2 production, indicating that they inhibited DR4-restricted T cell activation. FIG. 7A shows the effects of coincubating irradiated 3838 or D3 Priess cells with collagen peptide CII 261-273 (SEQ ID NO: 3) at the fixed concentration of 40 µg/ml, and with varying concentrations of polypeptides, for 2 hr at 37° C.

FIG. 7B shows the effects of incubating L cells transfected with a gene encoding HLA-DR4 with collagen peptide CII 261-273 (SEQ ID NO: 3) at the fixed concentration of 40 µg/ml, and with varying concentrations of GAL, TAL, GTL, TGA, and Copolymer 1, for 2 hr at 37° C. T cells were then added (clones 3838 or D3 as indicated), and samples were further incubated for 24 hr at 37° C. Supernatants (30 µl) were then removed, and were assayed for activation by IL-2-induced proliferation of IL-2-dependent cytotoxic T lymphocytes (CTL-L). Each polypeptide mixture was tested in duplicate. The concentration of the present polypeptides is indicated on the abscissa. The extent of inhibition by TAL is shown as solid circles (●), by TGA as solid triangles (▲), by GTL as open triangles(Δ), and by Copolymer 1 as solid squares (■). Percent inhibition of CTL-L proliferation shown on the ordinate was calculated using equation 1.

EXAMPLE 10

Copolymer 1 Inhibits Activation of T Cells Responsive to a Myasthenia Gravis Antigenic Peptide Methods Copolymer 1

Copolymer 1 was obtained from Teva Pharmaceutical Industries (Petach Tikva, Israel).

Myasthenia Gravis-Related Peptides were synthesized on an Applied Biosystems Peptide Synthesizer using solid phase techniques. Barany et al., THE PEPTIDES 1 (1979). Peptides were purified by reversed-phase HPLC. The peptides used were the p259 peptide, see Zisman et al., *Hum. Immuol.* November 1995; 44(3):121-30; Brocke et al., *Immunology*; April 1990; 69(4):495-500.

IL-2 Secretion

Secretion of IL-2 by the cell line WCB AB in response to the myasthenia gravis peptides and/or Copolymer 1 were evaluated. Cells ($1.5 \times 10^4$) were incubated with the indicated antigen. Secretion of IL-2 by the cell line WCB AB was used as a measure of activation of that T cell line.

Results

Table 9 indicates that the p259 peptide stimulates T cell secretion. However, when Copolymer 1 is incubated with the p259 peptide, T cell secretion of IL-2 is inhibited in a dose-related fashion. At 100 μM Copolymer 1 inhibits about 91% of IL-2 secretion (Table 10), indicating that Copolymer 1 is a potent inhibitor of T cell activation.

TABLE 9

IL-2 secretion from WCB AB line in response to p259

| p 259 conc. (μM) | Avg OD (450 nm) | SD | % CV | IL-2 (pg/ml) |
|---|---|---|---|---|
| 0 | 0.077 | 0.01 | | 0 |
| 0.25 | 0.135 | 0.00 | | 24 |
| 0.5 | 0.227 | 0.01 | 3.9 | 72 |
| 1 | 0.387 | 0.01 | 2.9 | 159 |
| 2 | 0.725 | 0.02 | 2.4 | 347 |

TABLE 10

IL-2 secretion from WCB AB line in response to Cop1 alone or 2μM p259 + Cop1

| Cop1 (μM) | Avg OD (450 nm) | SD | % CV | IL-2 (pg/ml) | % Inhibition |
|---|---|---|---|---|---|
| 0 | 0.725 | 0.02 | 2.4 | 347 | |
| 1 | 0.086 | 0.01 | | 0 | |
| 2 | 0.079 | 0.00 | | 0 | |
| 10 | 0.086 | 0.00 | | 0 | |
| 20 | 0.266 | 0.01 | 8.0 | 93 | 73 |
| 60 | 0.166 | 0.01 | | 40 | 88 |
| 100 | 0.151 | 0.01 | 11.2 | 32 | 91 |

Absorbance is the average of 3 samples. Confidence values were calculated relative to the absorbance of a blank (% CV = SD/(Avg − blank) *100).

What is claimed:

1. A pharmaceutical composition comprising a pharmaceutically acceptable carrier and an amount of a mixture of terpolymers, each terpolymer consisting of tyrosine, alanine and lysine.

2. The pharmaceutical composition of claim 1, wherein said tyrosine is present in a mole fraction of about 0.005 to about 0.250; said alanine is present in a mole fraction of about 0.3 to about 0.6; and lysine is present in a mole fraction of about 0.1 to about 0.5.

3. The pharmaceutical composition of claim 1, wherein said tyrosine is present in a mole fraction of 0.10, said alanine is present in a mole fraction of 0.54, and said lysine is present in a mole fraction of 0.35.

4. The pharmaceutical composition of claim 1 wherein said mixture of terpolymers has an average molecular weight of about 2,000 to about 40,000 daltons.

5. The pharmaceutical composition of claim 1 wherein said mixture of terpolymers has an average molecular weight of about 4,000 to about 9,000 daltons.

* * * * *

SEQUENCE LISTING

<160> NUMBER OF SEQ ID NOS: 3

<210> SEQ ID NO 1
<211> LENGTH: 19
<212> TYPE: PRT
<213> ORGANISM: Artificial Sequence
<220> FEATURE:
<223> OTHER INFORMATION: synthetic peptide (MBP residues 84-102)

<400> SEQUENCE: 1

Asp Glu Asn Pro Val Val His Phe Phe Lys Asn Ile Val Thr Pro Arg
1               5                   10                  15

Thr Pro Pro
        19

<210> SEQ ID NO 2
<211> LENGTH: 13
<212> TYPE: PRT
<213> ORGANISM: Artificial Sequence
<220> FEATURE:
<223> OTHER INFORMATION: synthetic peptide (HA residues 306-318)

```
-continued

<400> SEQUENCE: 2

Pro Lys Tyr Val Lys Gln Asn Thr Leu Lys Leu Ala Thr
 1               5                  10          13

<210> SEQ ID NO 3
<211> LENGTH: 13
<212> TYPE: PRT
<213> ORGANISM: Artificial Sequence
<220> FEATURE:
<223> OTHER INFORMATION: synthetic peptide (CII amino acids 261-273)

<400> SEQUENCE: 3

Ala Gly Phe Lys Gly Glu Gln Gly Pro Lys Gly Glu Pro
 1               5                  10          13
```